United States Patent
Glawdel et al.

(10) Patent No.: US 11,406,271 B2
(45) Date of Patent: Aug. 9, 2022

(54) DUAL SENSOR SYSTEM FOR CONTINUOUS BLOOD PRESSURE MONITORING DURING TRANSCATHETER HEART VALVE THERAPIES

(71) Applicant: Three Rivers Cardiovascular Systems Inc., Toronto (CA)

(72) Inventors: Tom Glawdel, Toronto (CA); Christopher Glover, Toronto (CA); Eric Caron, Toronto (CA); Sylvain Abel, Shawinigan (CA)

(73) Assignee: HemoCath Ltd., Toronto (CA)

( * ) Notice: Subject to any disclaimer, the term of this patent is extended or adjusted under 35 U.S.C. 154(b) by 142 days.

(21) Appl. No.: 16/764,119

(22) PCT Filed: Nov. 13, 2018

(86) PCT No.: PCT/CA2018/051430
§ 371 (c)(1),
(2) Date: May 14, 2020

(87) PCT Pub. No.: WO2019/095049
PCT Pub. Date: May 23, 2019

(65) Prior Publication Data
US 2020/0390350 A1 Dec. 17, 2020

Related U.S. Application Data

(60) Provisional application No. 62/585,757, filed on Nov. 14, 2017.

(30) Foreign Application Priority Data

Oct. 23, 2018 (CA) ................................ CA 3021877

(51) Int. Cl.
*A61B 5/0215* (2006.01)
*A61B 90/00* (2016.01)
(Continued)

(52) U.S. Cl.
CPC ........ *A61B 5/02154* (2013.01); *A61B 5/6851* (2013.01); *A61B 5/6857* (2013.01);
(Continued)

(58) Field of Classification Search
None
See application file for complete search history.

(56) References Cited

U.S. PATENT DOCUMENTS

2014/0249386 A1* 9/2014 Caron ...................... A61B 5/01
600/301
2017/0027458 A1* 2/2017 Glover ................... G16H 20/40

FOREIGN PATENT DOCUMENTS

| CA | 2849717 | 5/2013 |
| CA | 2954959 | 1/2016 |

OTHER PUBLICATIONS

Melamud et al., "Development of an SU-8 Fabry-Perot Blood Pressure Sensor", 18th IEEE International Conference on Micro Electro Mechanical Systems, 2005, MEMS 2005 (Year: 2005).*
(Continued)

*Primary Examiner* — Yi-Shan Yang
(74) *Attorney, Agent, or Firm* — Miltons IP/p.i.

(57) ABSTRACT

Dual sensor system for continuous blood pressure monitoring during transcatheter heart valve therapies (TVT), such as transcatheter aortic valve replacement (TAVR) or transcatheter mitral valve replacement (TMVR), comprises a controller, a support guidewire for TVT containing a first Fabry-Pérot (FP) optical pressure sensor near its distal end, and a pigtail catheter for delivery of contrast medium containing a second FP optical pressure sensor near its distal end. For example, for TAVR, the support guidewire is positioned to place the first optical pressure sensor within the left ventricle (LV) for monitoring LV pressure, the pigtail catheter is positioned in the aorta to place the second optical pressure sensor in the ascending aorta for direct measure-
(Continued)

ment of pressure in the aorta, downstream of the aortic valve, enabling continuous monitoring of blood pressure at both sensor locations during TAVR. The controller may be configured to interface with standard patient monitoring systems.

32 Claims, 19 Drawing Sheets

(51) Int. Cl.
*A61B 5/00* (2006.01)
*A61F 2/24* (2006.01)
(52) U.S. Cl.
CPC ............ *A61B 90/39* (2016.02); *A61F 2/2427* (2013.01); *A61B 2090/3966* (2016.02); *A61B 2562/0266* (2013.01)

(56) References Cited

OTHER PUBLICATIONS

Melamud, R. et al.; "Development of an SU-8 Fabry-Perot blood pressure sensor"; Micro Electro Mechanical Systems, 2005. MEMS 2005. 18th IEEE International Conference on. IEEE, 2005; 4 pages.
International Search Report issued on International Patent Application No. PCT/CA2018/051430; dated Jan. 22, 2019.

* cited by examiner

A-A CROSS-SECTION VIEW OF FIG. 2

B-B CROSS-SECTION VIEW OF FIG. 2

C-C CROSS-SECTION VIEW OF FIG. 2

A-A CROSS-SECTION VIEW OF FIG. 2

B-B CROSS-SECTION VIEW OF FIG. 2

C-C CROSS-SECTION VIEW OF FIG. 2

D-D CROSS-SECTION VIEW OF FIG. 2

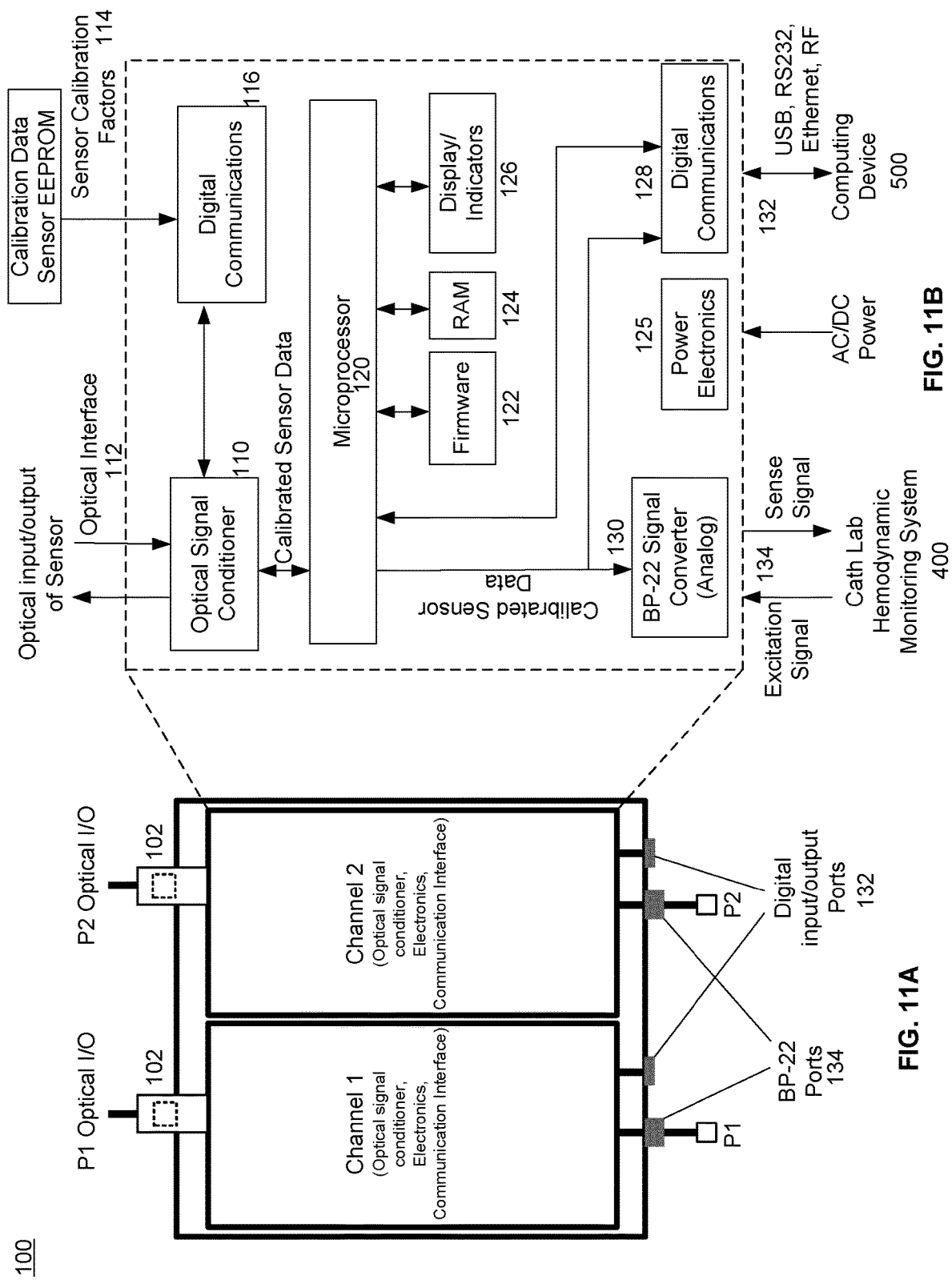

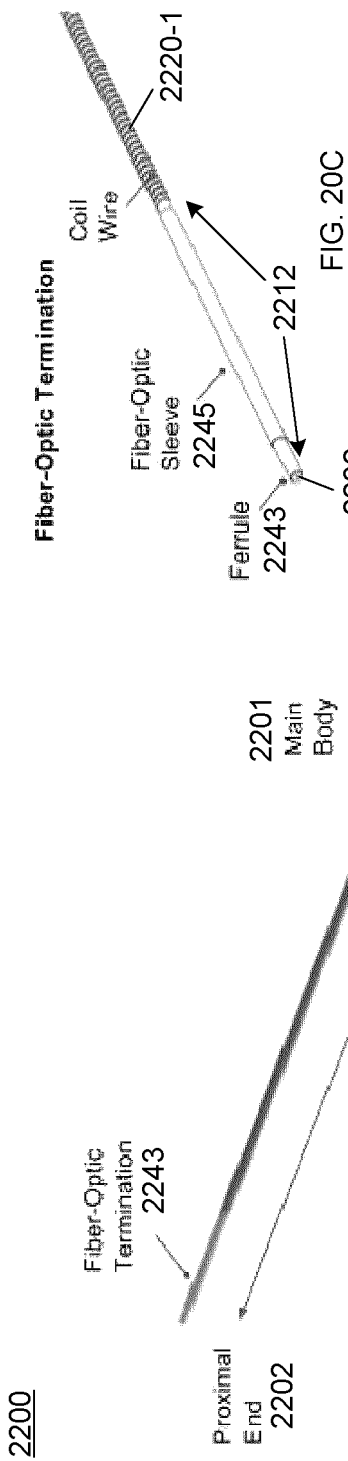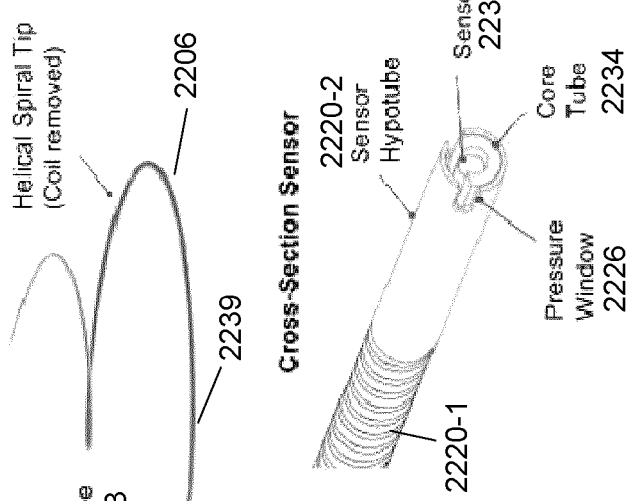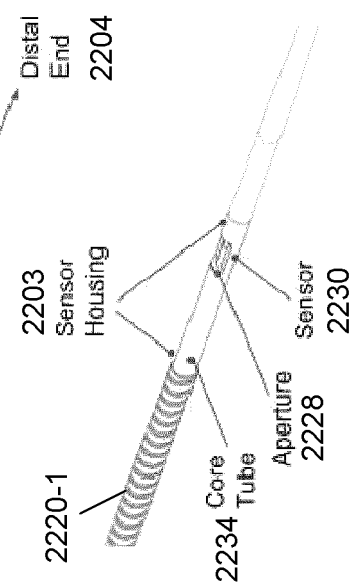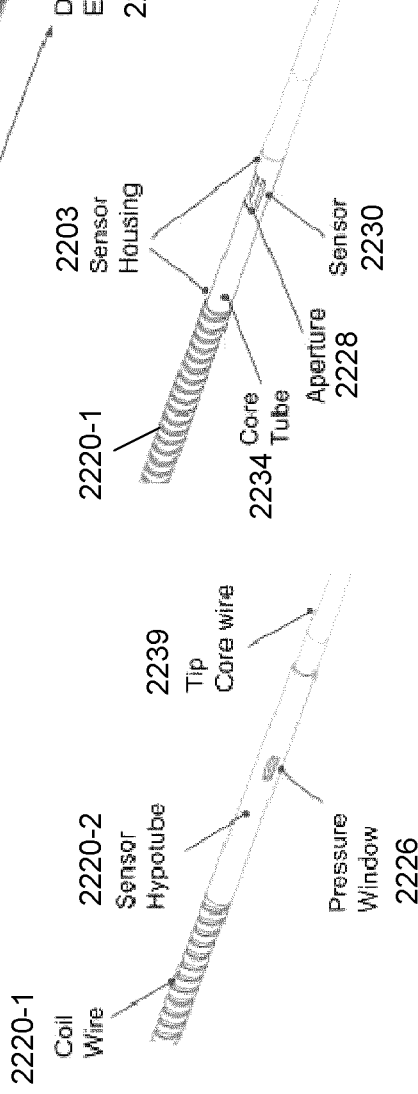

DUAL SENSOR SYSTEM FOR CONTINUOUS BLOOD PRESSURE MONITORING DURING TRANSCATHETER HEART VALVE THERAPIES

CROSS-REFERENCE TO RELATED APPLICATIONS

This application claims priority from U.S. provisional Patent Application 62/585,757, filed Nov. 14, 2017, entitled "Dual Sensor System for Continuous Blood Pressure Monitoring During Transcatheter Heart Valve Therapies", which is incorporated herein by reference in its entirety.

This application is related to U.S. patent application Ser. No. 15/293,380, filed Oct. 14, 2016, entitled "System and Apparatus comprising a Multi-Sensor Catheter for Right Heart and Pulmonary Artery Catheterization", which is a Continuation in Part of U.S. patent application Ser. No. 14/874,604, filed Oct. 5, 2015 (now U.S. Pat. No. 9,504,392), which is a Continuation of U.S. patent application Ser. No. 14/354,624, filed Apr. 28, 2014 (now U.S. Pat. No. 9,149,230), which is a national stage entry of PCT International Application No. PCT/IB2012/055893, entitled "Apparatus, system and methods for measuring a blood pressure gradient", filed Oct. 26, 2012, which claims priority from U.S. Provisional patent application No. 61/552,778 entitled "Apparatus, system and methods for measuring a blood pressure gradient", filed Oct. 28, 2011 and from U.S. Provisional patent application No. 61/552,787 entitled "Fluid temperature and flow sensor apparatus and system for cardiovascular and other medical applications", filed Oct. 28, 2011.

This application is related to U.S. patent application Ser. No. 15/001,347, filed Jan. 20, 2016, entitled "System and Apparatus Comprising a Multisensor Guidewire for Use in Interventional Cardiology", which is a Continuation-in-Part of PCT International Application No. PCT/IB2015/055240, of the same title, filed Jul. 10, 2015, designating the United States; this application is also related to U.S. patent application Ser. No. 15/326,134 filed Jan. 13, 2017, which is a national stage entry of PCT International Application No. PCT/IB2015/055240; PCT/IB2015/055240 claims priority from U.S. Provisional patent application No. 62/023,891, entitled "System And Apparatus Comprising a Multisensor Support Guidewire for Use in Trans-Catheter Heart Valve Therapies", filed Jul. 13, 2014 and from U.S. Provisional patent application No. 62/039,952, entitled "System and Apparatus Comprising a Multisensor Support Guidewire for Use in Trans-Catheter Heart Valve Therapies", filed Aug. 21, 2014.

TECHNICAL FIELD

The present invention relates to a system and apparatus for continuous monitoring of blood pressure using optical pressure sensors contained within a guidewire or a catheter for minimally invasive interventional cardiology, including real-time blood pressure measurements during transcatheter heart therapies, such as transcatheter heart valve replacement.

BACKGROUND

Percutaneous procedures for minimally invasive transcatheter heart valve diagnosis, repair and replacement avoid the need for invasive open-heart surgery. These minimally invasive procedures may be referred to as Transcatheter Valve Therapies (TVT). For example, when a heart valve is found to be malfunctioning because it is defective or diseased, minimally invasive methods are known for repair and replacement of the heart valve, by introduction of a guidewire and catheter intravascularly into the heart, e.g. to access a heart valve and one or more chambers of the heart. The guidewire and catheter are then used to guide components into the heart for TVT.

TVT for valve repair includes, for example, procedures such as, balloon aortic valvuloplasty (BAV), to widen an aortic valve which is narrowed by stenosis, or insertion of a mitral clip to reduce regurgitation when a mitral valve fails to close properly. Alternatively, if the valve cannot be repaired, a prosthetic replacement valve may be introduced. Minimally invasive Transcatheter heart Valve Replacement (TVR) procedures, including Transcatheter Aortic Valve Implantation/Replacement (TAVI or TAVR) and Transcatheter Mitral Valve Implantation/Replacement (TMVI or TMVR), have been developed over the last decade and have become more common procedures in recent years. For example, it has been reported that the TAVR market is projected to grow at 21% Compound Annual Growth Rate (CAGR) over the next 5 years, to about 120,000 TAVR procedures per years in the United States.

As experience with TVT continues to evolve, interventional cardiologists who perform TVT procedures provide feedback on existing systems and apparatus and continue to seek improved or alternative systems and apparatus to advance TVT, including diagnostic tools comprising optical pressure sensors that provide real-time direct measurements within the heart of important hemodynamic cardiovascular parameters before, during and after TVT.

The above referenced related patents and patent applications disclose multi-sensor guidewires and multi-sensor micro-catheters for use in interventional cardiology; all these patents and applications are incorporated herein by reference in their entirety. For example, U.S. Pat. Nos. 9,504,392 and 9,149,230 disclose multi-sensor micro-catheters and multi-sensor guidewires in which a distal end portion contains multiple optical pressure sensors arranged for measuring blood pressure at several sensor locations, simultaneously, in real-time. The disclosed multi-sensor micro-catheters and multi-sensor guidewires can be configured for use in minimally invasive surgical procedures for measurement of intra-vascular pressure gradients, and more particularly, for direct measurement of a transvalvular pressure gradient within the heart, for any one of the four heart valves. For example, a transvalvular measurement of pressure across the aortic valve is made with a multi-sensor guidewire or multi-sensor catheter having optical pressure sensors positioned upstream and downstream of the aortic valve to measure pressure, in real-time, concurrently in the ascending aorta and left ventricle, allows for assessment of aortic valve regurgitation or stenosis, before and after a TAVR procedure.

TAVR procedures are carried out in a specialized operating room which is equipped for therapeutic and diagnostic procedures, including fluoroscopic imaging, echo-cardiographic imaging, and patient monitoring. For minimally invasive transcatheter procedures, this specialized operating room is typically referred to as a cardiac catheterization laboratory, or "Cath Lab". For example, a small incision is made into a femoral artery in the groin (transfemoral approach) or a radial artery in the arm (transradial approach) to allow for introduction of guidewires and catheters, which are advanced through the aorta and into the left ventricle (LV) of the heart. Many components used during TAVR, such as catheters, support guidewires and valve delivery devices are single-use, disposable medical supplies. For this reason, unit cost is an important consideration. For reasons of regulatory approval, and to promote user acceptance and early adoption, it is desirable that systems comprising sensor guidewires and sensor catheters are based on related predicate devices and integrate within existing procedures, e.g. they can be manufactured from materials already approved for medical use and deployed in a similar manner to existing guidewires and catheters for TAVR. Another consideration for reducing cost and ease of use is compatibility with existing operating room equipment, such as patient monitoring and display systems.

The present invention seeks to provide an improved or alternative multi-sensor system and apparatus comprising optical pressure sensors for direct blood pressure measurement within the heart, e.g., for measurement of transvalvular pressure gradients during TVT, that provide for unit cost reduction, or mitigate one or more of the above-mentioned issues, or provide an alternative solution.

SUMMARY OF INVENTION

Aspects of the present invention provide a system and apparatus for monitoring of blood pressure at two locations for use during transcatheter valve therapies (TVT) and for related diagnostic measurements of hemodynamic parameters to assess heart valve function.

One aspect of the invention provides a dual sensor system for monitoring blood pressure at first and second locations during transcatheter valve therapy (TVT), comprising:
a controller;
a sensor support guidewire for TVT comprising a tubular member having a length extending between a proximal end and a distal end, the distal end comprising an atraumatic pre-formed curved flexible distal tip, the tubular member containing a first optical fiber extending within the sensor support guidewire from an optical input/output connector at the proximal end of the sensor support guidewire to a first Fabry-Pérot (FP) optical pressure sensor, the first FP optical pressure sensor being positioned within a distal region of the tubular member, near the distal tip, and a sensor aperture in the sensor support guidewire adjacent the first FP optical pressure sensor for fluid contact therewith;
a sensor angiographic catheter comprising a length of multi-lumen catheter tubing extending between a proximal end and a distal end and comprising a first lumen and a second lumen, the distal end comprising a preformed pigtail distal tip, and the catheter tubing having at its proximal end a connection hub comprising a first port for the first lumen and a second port for the second lumen, a second optical fiber extending within the first lumen from an optical input/output connector of the first port to a second FP optical pressure sensor, the second FP optical pressure sensor being positioned within a distal region of the first lumen near the distal tip, and a sensor aperture in the sensor catheter near the second FP optical pressure sensor for fluid contact therewith; the second port comprising an injection port for injection of fluid into the second lumen and the second lumen comprising a plurality of fluid apertures for fluid ejection along a length of the distal region between the sensor aperture and the distal tip;
the controller comprising an optical control unit (signal conditioner) comprising optical input/output ports for coupling to the optical input/output connectors of the sensor support guidewire and the sensor angiographic catheter; a light source and detector for operating the first and second FP optical pressure sensors and processing optical data from the first and second optical pressure sensors to generate data indicative of blood pressure; and a processor, memory, hardware and/or software components for generating analog and/or digital data comprising first and second pressure waveforms; and a communications interface comprising analog and/or digital ports for interfacing with at least one of a patient monitoring system and other peripherals.

The first and second FP optical pressure sensors are preferably two matched optical pressure sensors, i.e. a pair of similar FP Micro-Opto-Mechanical System (MOMS) sensors. These optical pressure sensors comprise, for example, standard optical fibers of 0.155 mm diameter and FP MOMS pressure sensors of 0.260 mm diameter at the sensor end of the optical fiber for sensing pressure. Smaller or bigger diameter optical fibers and sensors may be used as needed.

In the following description, the TVT support guidewire containing the first FP optical pressure sensor will be referred to as the 'TVT sensor support guidewire' or simply the 'sensor guidewire" and the angiographic catheter containing the second FP optical pressure sensor will be referred to as the 'sensor angiographic catheter' or simply the "sensor catheter".

In one embodiment, the system comprises a dual optical pressure sensor system which is configured to enable continuous direct monitoring of blood pressure in the left ventricle and in the ascending aorta, having applicability for measurements of hemodynamic parameters during TAVR. In this embodiment, the first FP optical pressure sensor (P1) is located near the atraumatic distal tip of the sensor support guidewire for positioning of P1 within the left ventricle during TAVR. For example, the flexible distal tip comprises a preformed curved tip and the first FP optical pressure sensor is positioned in a distal region of the sensor guidewire close to the flexible distal tip, or a few centimetres from the tip, to allow for placement of the FP optical pressure sensor in a central region of the left ventricle. An atraumatic flexible tip, such as a preformed J-tip, spiral tip, or other curved tip, provides for anchoring of the distal end of the sensor guidewire firmly in the left ventricle during TAVR, while reducing risk of tissue trauma or perforation of the left ventricle.

The sensor catheter takes the form of a dual lumen pigtail catheter having a plurality of apertures in the second lumen near the pigtail tip for injection of contrast medium into the LV and the aorta, and the second FP optical pressure sensor (P2) is located in a distal region of the first lumen of the sensor catheter, a small distance from the pigtail tip for positioning of P2 in the ascending aorta, downstream of the aortic valve, during TAVR. For example, the second pressure sensor is positioned adjacent a sensor aperture in the first lumen about 2 to 7 cm from the pigtail tip of the sensor catheter, and a number of apertures, e.g. 5 to 12 apertures, in the second lumen are provided closer to the tip for distributed injection of contrast medium into the LV or the aorta near the aortic valve.

For example, for monitoring of an aortic transvalvular pressure gradient, the first and second FP optical pressure sensors are a pair of similar FP optical pressure sensors configured for measuring a blood pressure gradient across the aortic valve during TAVR in a range of 0 mmHg to 60 mmHg within ±10 mmHg or less.

In another embodiment, the dual sensor system is configured for measurements of hemodynamic parameters during TMVR, wherein: the first FP optical pressure sensor (P1) is a distance L1 from the flexible distal tip of the sensor support guidewire for positioning of P1 within a first heart chamber on one side of the mitral valve during TMVR; the second FP optical pressure sensor (P2) is located in a distal region of the first lumen of the sensor catheter, a distance L2 from the pigtail tip for positioning of P2 in a second heart chamber, on an opposite side of the mitral valve during TMVR; and said plurality of apertures in the second lumen near the pigtail tip are provided for injection of contrast medium into the second heart chamber.

For example, for monitoring of a mitral valve pressure gradient, the first and second FP optical pressure sensors are a pair of similar FP optical pressure sensors configured for measuring a blood pressure gradient across the mitral valve during TMVR in a range of 0 mmHg to 20 mmHg within ±2 mmHg or less.

In some embodiments, optical input/output connector of the sensor support guidewire comprises a flexible optical coupling which is connected to the proximal end of the sensor guidewire by a separable optical connector. For over-the-guidewire mounting of components, for example a valve delivery device during a TAVR, from the proximal end of the sensor guidewire, the optical connector comprises a micro-connector, wherein the sensor guidewire comprises a male part of the optical micro-connector having a diameter no greater than the outside diameter of the sensor guidewire. The sensor guidewire has physical characteristics required of a TAVR support guidewire. For example, typically, characteristics of a TAVR support guidewire include a high stiffness, (e.g. a flexural modulus similar to that of an Amplatz™ Extra Stiff or Super Stiff guidewire, Confida™ Brecker guidewire or Safari™ guidewire), a nominal/standard outside diameter of 0.89 mm (0.035 inch) and, for a transfemoral approach, a length of 260 mm to 300 mm to allow for over-the-guidewire mounting of a valve delivery device and valve components. The flexible optical coupling provides a low cost optical connection (e.g. a simple optical fiber cable) that extends from the female part of the optical micro-connector, that forms a connector handle, to an optical connector at the proximal end of the flexible optical coupling for connection to the controller.

In some embodiments, the sensor catheter has the form of a conventional small diameter pigtail catheter used to inject a measured volume (bolus) of contrast agent into the aorta or LV through a plurality of apertures in the sensor catheter near the aortic valve, to allow fluoroscopic imaging of blood flow in the region of the aortic valve and for imaging to check for aortic regurgitation. The sensor catheter is a multi-lumen catheter, for example a dual lumen catheter with a port for each lumen. The first lumen accommodates the second FP optical pressure sensor and its optical fiber, and a second lumen provides for fluid injection of contrast agent, saline solution, or other fluids. Thus, the proximal end of the dual-lumen sensor catheter comprises a connection hub, through which each lumen of the multi-lumen sensor catheter is connected through a length of flexible tubing to the corresponding individual proximal port. One proximal port is provided for the optical input/output connector for the optical pressure sensor, and one proximal port is provided for connection to a fluid delivery injector for injection of contrast agent. For example, the sensor catheter has an outside diameter of 4 to 7 French, e.g., 5 French (1.7 mm/0.066 inch), and the second lumen has a diameter large enough to allow for rapid injection of a bolus of contrast medium, e.g. ~1 mm diameter. The second lumen may also be sized to allow for the introduction of a guidewire for insertion of the sensor catheter into the aorta or other blood vessel over the guidewire. The first lumen can be smaller, i.e. sized to accommodate the second optical fiber and the second optical pressure sensor, e.g. ~0.3 mm diameter.

Optionally, the sensor catheter may comprise one or more additional lumens, and the connection hub comprises a corresponding number of ports, for other purposes.

The sensor support guidewire may comprise a marker near the FP optical pressure sensor to assist in positioning the FP optical pressure sensor in use, e.g. radiopaque markers that can be visualized by conventional radio-imaging techniques. A marker is provided near the FP optical pressure sensor in the sensor catheter, and a marker may be provided at the distal tip of the sensor catheter. If required, markers may also be placed at regular intervals along the length of the sensor catheter and sensor guidewire, so that, in use, relative positioning or spacing of the FP optical pressure sensors of the sensor catheter and the sensor guidewire can be determined.

Embodiments of the system and apparatus of the present invention, comprising dual FP optical pressure sensors, provide for continuous direct monitoring of blood pressure at two locations, e.g. within the aorta and left ventricle, or within two chambers of the heart, for diagnostic measurements during TVT procedures, such as TAVR or TMVR, including e.g., measurements of transvalvular pressure gradients before, during and after deployment of a prosthetic heart valve.

In an embodiment, the controller comprises an optical control unit, which may be referred to as a signal conditioner, comprising a light source and detector, and an optical interface for coupling, via respective optical input/output ports, to each of the optical fibers and FP optical pressure sensors of the sensor catheter and the sensor support guidewire; data storage and processing means configured for processing optical data indicative of pressure values, and outputting digital and/or analog signals to ports of a communications interface, for coupling to a patient monitoring system and other peripherals, such as those typically found in a Cath Lab, to display pressure waveforms and associated hemodynamic data derived from the pressure data. For example, where a patient monitoring system or patient care monitor (PCM) is configured for receiving analog signals indicative of blood pressure compliant with the ANSI BP-22 Standard, the system controller comprises a BP-22 signal converter that provides ports for respective analog signal outputs from each of the two FP optical pressure sensors, together with the required control signals, i.e. the excitation signal output and sense signal input. The optical control unit comprising the signal conditioner may be integrated with, or be a separate module, from the interface/link unit which converts digital outputs from the optical control unit to provide said analog signals. Additionally, or alternatively, the optical control unit comprises ports for digital inputs and outputs, e.g. for wired or wireless coupling of the controller to a digital patient monitoring system and other peripherals, such as a network device or user device, e.g., a server, personal computer, or tablet which provides a user interface and/or data storage and analysis.

For a system configured for left heart catheterization, e.g. TAVR, in addition to displaying pressure waveforms from the aorta and the left ventricle, the system may provide for display a plurality of numeric values such as peak pressures, mean pressures, peak-to-peak pressure differentials for each curve, and pressure differentials or gradients, e.g., between the aorta and the left ventricle. The system may also compute a parameter such as an aortic regurgitation index (ARi), and display the ARi value in real time. Where the controller comprises an analog interface providing blood pressure signals to a BP-22 compliant patient monitoring system, display of pressure waveforms, analysis of data and display of related numeric data and parameters may be performed by the patient monitoring system.

Another aspect of the invention provides a computer program product embodied as a non-transient computer readable medium storing instructions, for execution in a processor of a controller for a dual sensor apparatus comprising a sensor guidewire containing a first FP optical pressure sensor and a sensor catheter containing a second FP optical pressure sensor, for processing optical data received concurrently from the first and second FP optical pressure sensors, said optical data being indicative of blood pressure. Optionally, said instructions further provide for processing and displaying, on a graphical user interface, pressure waveforms and numeric data relating to selected hemodynamic parameters and indexes.

Another aspect of the invention provides a sensor support guidewire for interventional cardiology comprising a tubular member having a length extending between a proximal end and a distal end, the distal end comprising a flexible distal tip, the tubular member containing an optical fiber extending within from an optical input/output connector at the proximal end of the sensor guidewire to a first FP optical pressure sensor, the first FP optical pressure sensor being positioned within a distal region of the sensor guidewire, near the distal tip, and a sensor aperture in the tubular member adjacent the first optical pressure for fluid contact therewith. In some embodiments the tubular member comprises an outer tubular member (outer tube) and an inner tubular member (inner tube or core tube), the inner tubular member being inserted within the outer tubular member. The inner and outer tubular members of this "tube-in-tube" construction are configured to provide required physical characteristics along the length of the sensor guidewire, e.g., stiffness, flexibility, and torque characteristics.

For use as a support guidewire for TVT, e.g. for TAVR or TMVR, the sensor guidewire is a stiff guidewire, e.g. having a stiffness similar to that of a standard support guidewire, such as an Amplatz™ Super Stiff support guidewire. A stiff distal region of the sensor guidewire provides a rail that can support a valve delivery device and valve components mounted over the TVT sensor support guidewire, i.e. for "over-the-guidewire" delivery and deployment.

For example, in the support guidewire, the first FP optical pressure sensor and its optical fiber are inserted into the inner tubular member, which may comprise a first stainless steel hypotube having physical characteristics providing a predetermined stiffness and flexibility to act as a core of the sensor guidewire, and then the inner tubular member is inserted into the outer tubular member. The outer tubular member may comprise one of: a second stainless steel hypotube which is more flexible (e.g. a laser cut hypotube); a flexible spiral wound micro-coil; and a combination thereof. In an embodiment, the inner tubular member acts as a core tube to provide a required stiffness along the length of the sensor guidewire, and the outer tubular member may be more flexible along most of its length. At the sensor position, where the inner tubular member has an aperture or is partially cut away to form an opening or cavity around the optical pressure sensor, the outer tubular layer, which itself has sensor aperture, comprises a reinforced stiffer region around the sensor aperture adjacent to the sensor.

The tube-in-tube construction facilitates fabrication of the sensor guidewire. For example, where the sensor guidewire comprises an inner tube and a more flexible outer tube, the optical fiber and FP optical pressure sensor are inserted into the inner tube from an opening at the distal end or through the sensor aperture, and the fiber is adhesively secured within the inner tube near the sensor to hold the sensor in the sensor location adjacent the aperture for fluid contact. The FP optical pressure sensor and its fiber is then protected within the inner tube while the inner tube is inserted into the more flexible outer tube.

The atraumatic flexible tip of the sensor guidewire may comprise an outer flexible coil wire and an inner core wire, which are configured to provide a desired flexibility and shape. The flexible tip may have a pre-formed curved shape, such as a spiral tip. If the components of the flexible tip are not formed integrally with the inner and/or outer tubular layers, the components of the flexible tip may be attached to the inner and/or outer tubular layers by suitable means, such as one or more of adhesive bonding, soldering, brazing, and welding, to provide a smooth transition between the sensor region of the sensor guidewire and the flexible tip. The flexible tip may have the same outer diameter as the sensor region of the sensor guidewire, or the tip may taper to a smaller diameter.

In some embodiments, the sensor guidewire further comprises a second optical pressure sensor and second optical fiber contained within the inner tubular member, the second optical pressure sensor being positioned proximally of the first optical pressure sensor. In a dual sensor guidewire, adjacent to each FP optical pressure sensor position, the inner tubular member has an aperture or is partially cut away to form a cavity around the optical pressure sensor, and the outer tubular layer comprises a stiffer, reinforced region around the aperture adjacent to each sensor. In an embodiment, the dual sensor guidewire may be configured for TAVR or TMVR.

Another aspect of the invention provides an angiographic sensor catheter comprising a length of multi-lumen catheter tubing extending between a proximal end and a distal end and comprising first and second lumens, the distal end comprising a preformed distal tip, the catheter tubing having at its proximal end a connection hub comprising corresponding a first port for the first lumen and a second port for second lumen; the first port for the first lumen providing an optical input/output connector, an optical fiber extending within the first lumen from the optical input/output connector to an FP optical pressure sensor positioned within a distal region of the sensor catheter near the distal tip, and an aperture in the first lumen near the FP optical pressure sensor for fluid contact therewith; the second port comprising an injection port for injection of fluid into the second lumen, and the second lumen comprising a plurality of apertures near the distal tip, e.g. in a distal region between the sensor aperture and the distal tip.

Yet another aspect of the invention provides a kit comprising components for use with a dual sensor system for monitoring blood pressure at first and second locations during transcatheter valve therapy (TVT), comprising:

a first component comprising: a sensor support guidewire for TVT comprising a tubular member having a length extending between a proximal end and a distal end, the distal end comprising an atraumatic pre-formed curved flexible distal tip, the tubular member containing a first optical fiber extending within the support guidewire from an optical input/output connector at the proximal end of the support guidewire to a first Fabry-Pérot (FP) optical pressure sensor, the first FP optical pressure sensor being positioned within a distal region of the tubular member, near the distal tip, and a sensor aperture in the sensor guidewire adjacent the first optical FP pressure sensor for fluid contact therewith;

a second component comprising: a sensor angiographic catheter comprising a length of multi-lumen catheter tubing extending between a proximal end and a distal end and comprising a first lumen and a second lumen, the distal end comprising a preformed pigtail distal tip, and the catheter tubing having at its proximal end a connection hub comprising a first port for the first lumen and a second port for the second lumen, a second optical fiber extending within the first lumen from an optical/input output connector of the first port to a second FP optical pressure sensor, the second FP optical pressure sensor being positioned within a distal region of the first lumen near the distal tip, and a sensor aperture in first lumen of the catheter tubing near the FP optical pressure sensor for fluid contact therewith; the second port comprising an injection port for injection of fluid into the second lumen, and the second lumen comprising a plurality of fluid apertures along a length of the distal region between the sensor aperture and the distal tip; and wherein the first and second FP optical pressure sensors are pair of similar FP optical pressure sensors.

For example, the first and second FP optical pressure sensors are configured for measuring a transvalvular blood pressure gradient across an aortic valve during TAVR, in a range of 0 mmHg to 60 mmHg within ±10 mmHg or less. As another example, the first and second FP optical pressure sensors are configured for measuring a transvalvular blood pressure gradient across a mitral valve during TMVR, in a range of 0 mmHg to 20 mmHg within ±2 mmHg or less.

Thus, systems and apparatus comprising dual FP optical pressure sensors according to embodiments of the present invention provide for diagnostic measurements and monitoring of hemodynamic parameters, including measurement of blood pressure concurrently and continuously at two different and variable locations, e.g. within the aorta and left ventricle during TAVR. Accordingly, dual sensor systems may be provided wherein the sensor locations are configured for use during other TVT, such as TMVR, BAV, or for diagnostic measurements during left heart catheterization.

The foregoing and other objects, features, aspects and advantages of the present invention will become more apparent from the following detailed description, taken in conjunction with the accompanying drawings, of embodiments of the invention, which description is by way of example only.

BRIEF DESCRIPTION OF THE DRAWINGS

In the drawings, identical or corresponding elements in the different Figures have the same reference numeral.

FIG. 11A shows a schematic block diagram of components of a controller comprising first and second channels for a dual sensor system of an embodiment such as illustrated in FIG. 1, comprising sensor inputs and digital and analog interfaces comprising BP-22 analog signal ports for coupling to a BP-22 compliant patient monitoring system and FIG. 11B shows a schematic block diagram showing details of components of one channel of the controller;

FIGS. 20A, 20B, 20C, 20D and 20E show views of a sensor support guidewire for TVT according to another embodiment, to show details of elements of a tube-in-tube construction for a single sensor support guidewire.

DETAILED DESCRIPTION

Dual Sensor System

Figure 1:
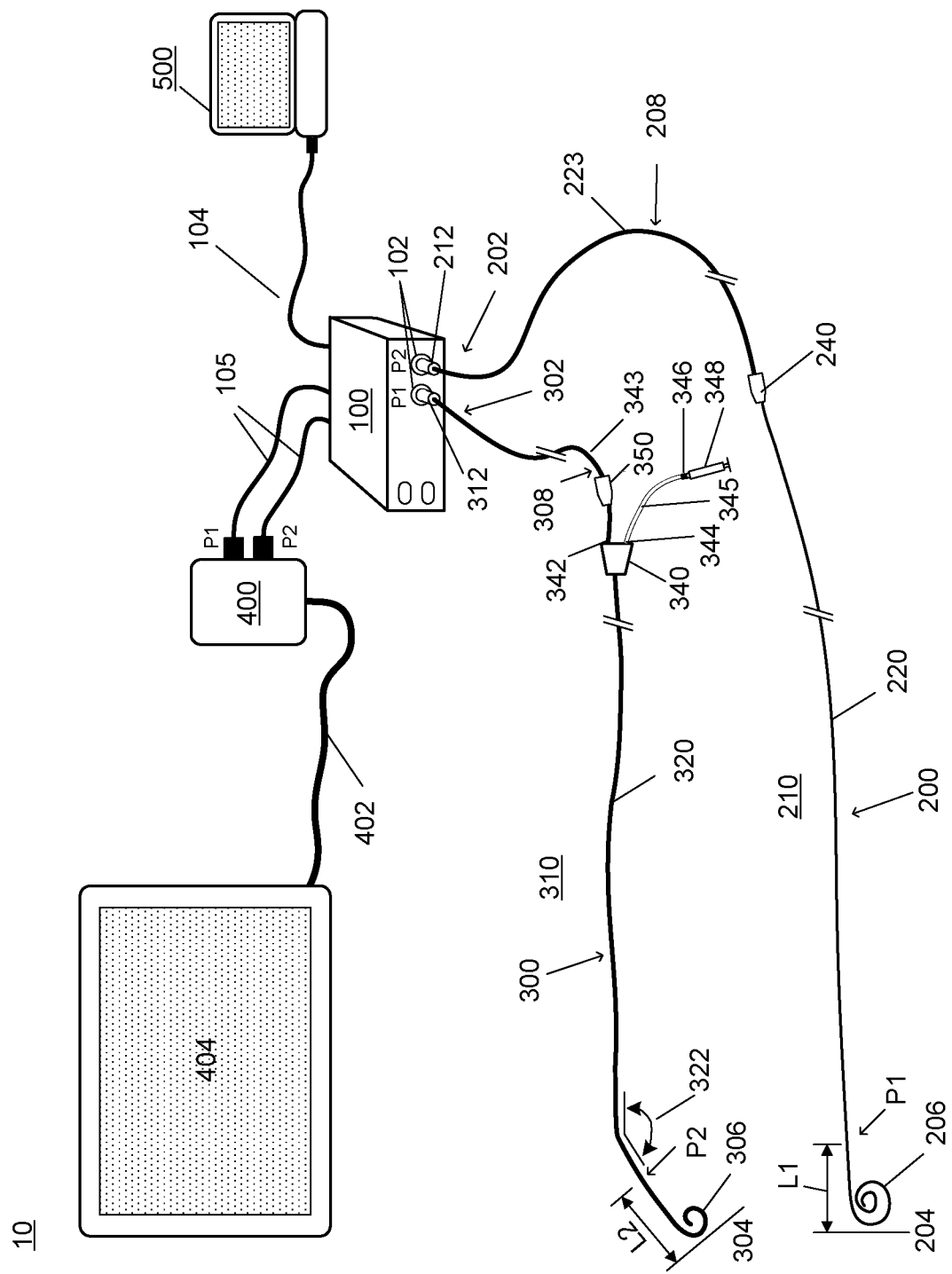
FIG. 1 illustrates schematically a system of a first embodiment, comprising a controller, a support guidewire containing a first Fabry-Perot (FP) optical pressure sensor (sensor support guidewire), a multi-lumen angiographic catheter containing a second FP optical pressure sensor (sensor catheter), wherein the sensor support guidewire and the sensor catheter are optically coupled to the controller, and the controller is connected to a patient monitoring system linked to a large screen display.

A schematic view of a dual sensor system 10 according to a first embodiment, configured for continuous blood pressure monitoring, e.g., during transcatheter heart valve replacement, is shown in FIG. 1. The dual sensor system 10 comprises a controller 100 to which is coupled to a TVT sensor support guidewire 200, a sensor angiographic catheter 300, and peripheral equipment, e.g., a patient monitoring system 400 and a user interface 500. The TVT sensor support guidewire 200 contains a first FP optical pressure sensor located at position P1, a distance L1 from the distal end 204 of the TVT sensor support guidewire, which comprises a flexible distal tip 206. The sensor angiographic catheter 300 is a multi-lumen catheter, e.g. a dual lumen catheter, containing in a first lumen a second FP optical pressure sensor, located at position P2, a distance L2 from distal end 304, and having a second lumen for fluid injection, and a pigtail tip 306. The TVT sensor support guidewire 200 is coupled to the controller 100 by an optical/input connector comprising a flexible optical coupling 208, e.g., comprising an optical fiber within flexible tubing 223 extending between optical connector 240 and optical connector 212. The sensor angiographic catheter 300 is coupled to the controller 100 by a flexible optical coupling 308, e.g., comprising an optical fiber within flexible tubing 343 extending between optical connector 350 and optical connector 312.

In the following detailed description, for conciseness, the TVT sensor support guidewire 200 containing the first FP optical pressure sensor will be referred to as the "sensor support guidewire", or simply the "sensor guidewire", and the sensor angiographic catheter 300 containing the second FP optical sensor will be referred to as the "sensor catheter".

The controller 100 comprises first and second optical connection ports 102 (i.e. 102-P1 and 102-P2) for optical connector 212 at the proximal end 202 of the flexible optical coupling 208 of the sensor guidewire 200 and optical connector 312 at the proximal end 302 of the flexible optical coupling 308 of the sensor catheter 300. The controller 100 also comprises a communication interface having analog and digital ports comprising outputs for the patient monitoring system 400, other peripherals, network devices and user devices, e.g., the user interface 500 which may, for example, be a personal computer (PC) or tablet PC connected through link 104. As illustrated schematically in FIG. 1, the control unit 100 is connected through electrical connections 105 to a patient monitoring system 400, which has a link 402 to a graphical display 404, such as one of the standard large screen monitors used in the Cath Lab or operating room. The monitoring system 400 may be part of a standard patient monitoring system, which may be referred to as a Patient Care Monitor (PCM), or it may be a dedicated stand-alone monitoring unit.

Referring to FIG. 1, the sensor guidewire 200 extends from the optical connector 240 at its proximal end to a distal end 204 comprising a soft flexible tip 206, such as a pre-formed atraumatic curved tip, e.g. a spiral tip. (That is, "proximal" and "distal" are referenced relative to the controller 100). The sensor guidewire 200 is detachably connected to the flexible optical coupling 208 by separable optical connector 240 at its proximal end. Near its distal end, the sensor guidewire 200 contains the first FP optical pressure sensor, at a location indicated by P1, and its optical fiber. The optical fiber extends from the optical sensor through the length of the sensor guidewire to the optical connector 240. A second optical fiber extends from the optical connector 240, through the flexible optical coupling 208 to the optical input/output connector 212 at the proximal end 202 of the assembly. The sensor guidewire 200 takes the form of a support guidewire for TAVR, i.e. it has suitable characteristics such as, stiffness, flexibility, torque characteristics, length and outside diameter to act as a support guidewire over which heart valve components may be delivered, as will be explained below in more detail with reference to FIGS. 2, 3A, 3B and 3C. The flexible optical coupling 208 does not need to have the same stiffness characteristics and provides a more flexible optical coupling (e.g. a simple optical cable) between the control unit 100 and the optical connector 240 for connection to the sensor guidewire 200. In use, for activation of the FP optical pressure sensor, the sensor guidewire 200 is optically coupled through the flexible optical coupling 208 to the corresponding optical input/output port 102-P2 of the optical control unit 100. The optical connector 240 is a separable optical connector so that the sensor guidewire 200 can be detachably connected to the flexible optical coupling 208, for activation as needed.

The sensor catheter 300 comprises a length of dual lumen catheter tubing extending from a connection hub 340 near its proximal end to a distal end 304 comprising a distal tip in the form of a preformed pigtail tip 306. The connection hub 340 comprises dual ports 342 and 344. The sensor catheter 300 has a form similar to a conventional multi-lumen catheter, in this case a dual lumen catheter, which will be described in more detail below with reference to FIGS. 4, 5A and 5B. The FP optical pressure sensor, indicated by position P2 is contained within the distal region of a first lumen and its optical fiber extends through the lumen, through the connection hub 340, and through a length of flexible tubing from the first port 342 to an optical input/output connector 350. A second lumen of the sensor catheter has a plurality of apertures in the distal region near the pigtail tip 306 and the second lumen coupled through connection hub 340 to a second port 344 comprising a length of flexible tubing 345 to a fluid port or connector 346 for coupling to a fluid injector 348, e.g. a syringe or pump. The flexible optical coupling 308 comprises a flexible optical cable 343 containing an optical fiber extending between the optical connector 350 and the control unit 100, i.e. proximal end 302 of the flexible optical coupling 308 is optically coupled via optical input/output connector 312 to port 102-P1 of the optical control unit 100. The separable optical connector 350 allows for the flexible optical coupling 308 to be disconnected while the pigtail catheter is inserted and used in the normal manner. Then, optical connector 350 is connected to the sensor catheter to activate the second FP optical pressure sensor when pressure measurements, e.g. in the aorta (Ao) are required. The port 344 at the proximal end which is coupled to the injector 348 provides for injection of contrast medium, or other fluid, through the second lumen of the sensor catheter 300 to a plurality of apertures distributed radially along a length of the distal region near the pigtail tip 306. The second lumen may also provide for passing of a guidewire for introduction of the sensor catheter over the guidewire into the aorta or other vessel. The pigtail sensor catheter 300 may be a straight catheter, or it may be a preformed angled pigtail catheter, e.g. having a 145° or 155° angle, as indicated by 322.

The TVT sensor support guidewire 200 and its input/output optical connector comprising the flexible optical coupling 208 may be referred to as the sensor guidewire assembly 210. The sensor angiographic catheter 300 and its input/output optical connector comprising the flexible optical coupling 308 may be referred to as the sensor catheter assembly 310.

Figure 2:
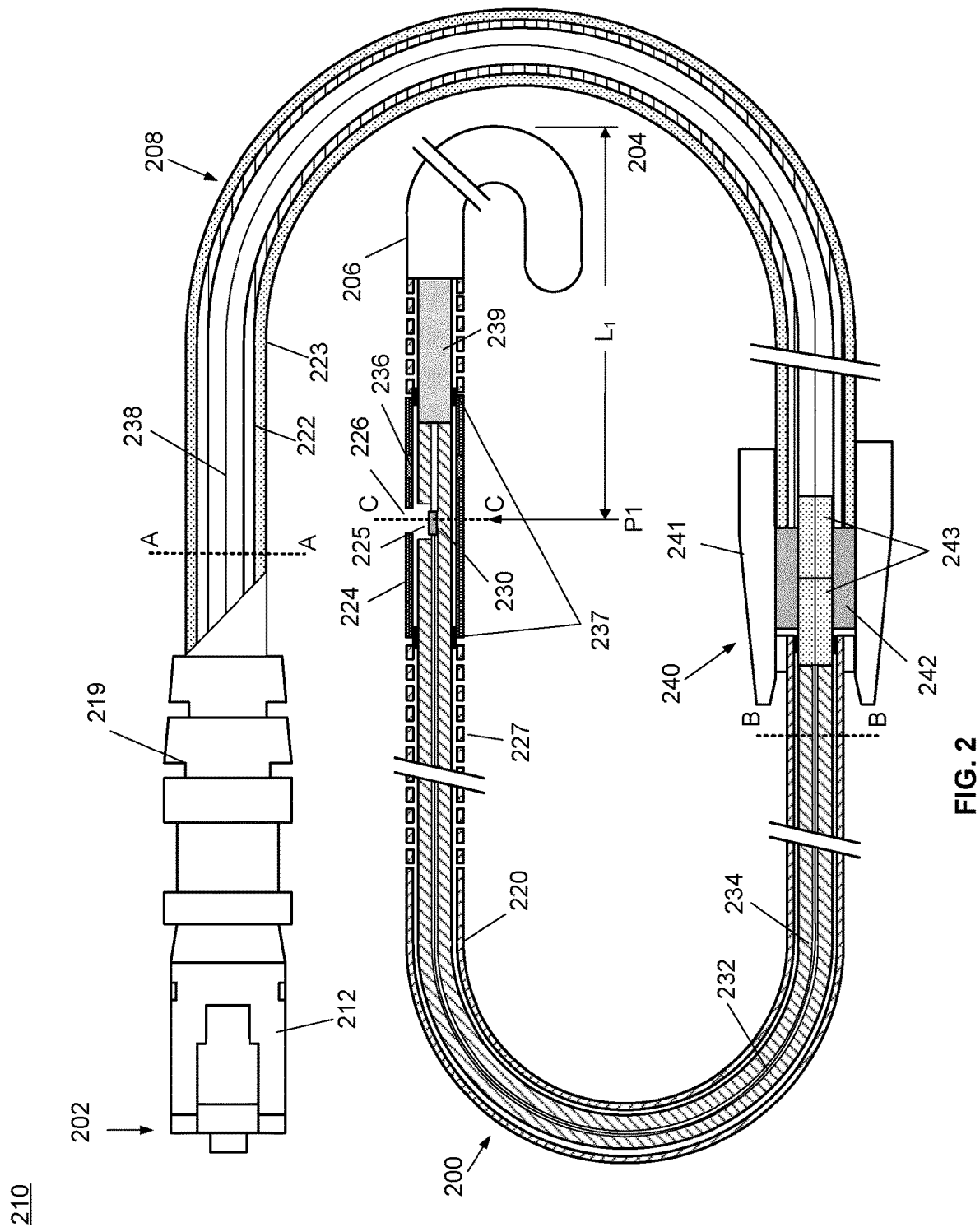
FIG. 2 shows an enlarged schematic longitudinal partial cross-sectional view of the sensor guidewire of the first embodiment, e.g., configured for measuring blood pressure in the left ventricle (LV) during TAVR.
Figure 3A:
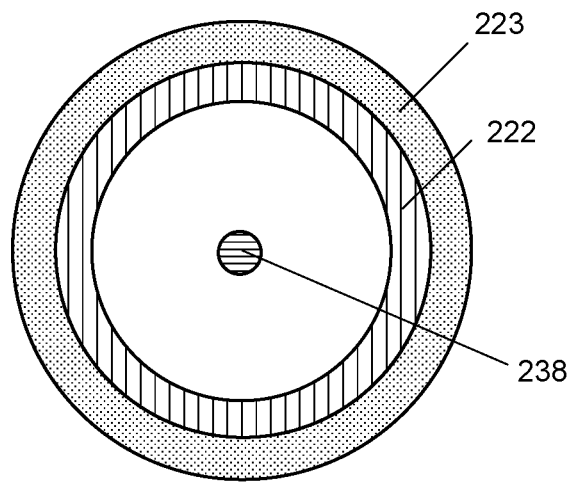
FIGS. 3A, 3B and 3C show enlarged axial cross-sectional views of the sensor guidewire illustrated in FIG. 2 taken, respectively, through planes A-A, B-B and C-C of FIG. 2.
Figure 3B:
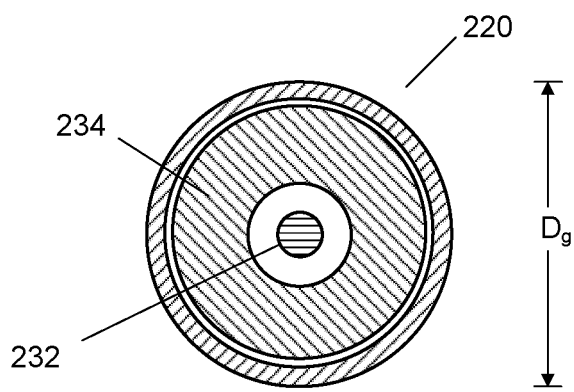
Figure 3C:
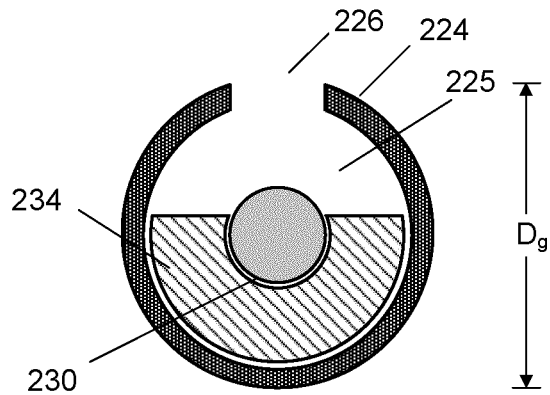

The TVT sensor support guidewire assembly 210 is illustrated in more detail in the schematic longitudinal cross-sectional view shown in FIG. 2, and in schematic cross-sectional views shown in FIGS. 3A, 3B and 3C. The sensor angiographic catheter assembly 310 is illustrated in more detail in the schematic longitudinal cross-sectional view shown in FIG. 4, and schematic cross-sectional views shown in FIGS. 5A and 5B.

TVT Sensor Support Guidewire

An enlarged schematic longitudinal partial cross-sectional view of the assembly 210 comprising a sensor guidewire 200 and a flexible optical coupling 208, of the first embodiment, is shown in FIG. 2. The sensor guidewire 200 is configured for measuring blood pressure, e.g. in the left ventricle (LV) during TAVR. The length of the sensor guidewire 200 extends from the separable optical connector 240 at its proximal end to the atraumatic flexible tip 206 at the distal end 204. The sensor guidewire 200 and the flexible optical coupling 208 are detachably connected by the separable optical connector 240. The sensor guidewire 200 comprises a flexible tubular member comprising an outer tubular layer 220 and an inner tubular layer 234. The structure and materials of the outer tubular covering 220 and the inner tubular layer 234 are selected to provide stiffness and other required physical characteristics of a support guidewire along its length. This tube-in-tube construction allows for the stiffness and other characteristics of the sensor guidewire 200 to be varied along its length between the optical connector 240 and the distal end 204 comprising the distal tip 206. For example, the inner tubular layer or core tube 234 comprises a stainless-steel hypotube which is relatively stiff and acts as a core for the outer tubular layer 220, which may be a more flexible stainless-steel hypotube or micro-coil. The first FP optical pressure sensor 230, at position P1, is optically and physically connected to the distal end (i.e. the sensor end) of the optical fiber 232, and the optical fiber 232 terminates at the proximal end (i.e. connector end) within the optical connector 240. At the sensor end of the fiber, a short length of protective tubing may be bonded around the sensor 230. The tubular layer 234 extends around the optical fiber 232 and extends beyond the sensor end of the fiber to toward the tip 206. In the region of the sensor 230, there is an aperture 226 in the outer tubular layer 220, and the inner tubular layer 234 is shaped to leave space around the sensor 230, e.g., has an aperture or is cut away to form a cavity 225, to accommodate the sensor 230 and to allow for fluid contact with the sensor 230. In this embodiment, the distal end portion of the tube-in-tube construction providing the tubular member comprises more flexible portions 227 of the outer tube 220, e.g. comprising a length of flexible stainless-steel micro-coil, and a reinforced stiffer section 224 of hypotube in between. As illustrated, the reinforced region 224 of the external tubular layer 220 extends a short length each side of the sensor position P1, to provide a required stiffness in the region of the sensor, i.e., where the stiffer inner tubular layer 234 is cut away to provide for fluid contact with the sensor. If required, a radiopaque marker 236 is provided near the sensor, to assist in positioning the sensor 230 in use, e.g., by fluoroscopic imaging. The inner tubular layer 234 extends a short distance past the sensor 230 and is bonded to the tip of core wire 239 of the flexible tip 206. For example, the flexible tip 206 comprises an outer flexible coil wire, and the tip core wire 239 has a ground profile along its length, i.e. is tapered to a smaller diameter, to progressively reduce stiffness of the flexible tip 206. To secure the sensor 230 in the sensor position P1 next to the aperture 226, the inner core tube 234 and outer tubular layer 220 may be secured to each other, e.g. by adhesive, filler or solder, at points 237 at each end of the reinforced region 224. The atraumatic flexible tip 206 may be a preformed J-tip, a preformed flat spiral tip, or a preformed 3-dimensional spiral or coiled tip, as will be described in more detail in subsequent paragraphs. A coating, such as a hydrophilic coating, may be provided along the length of the sensor guidewire.

The sensor guidewire 200 has physical characteristics along its length, e.g. stiffness, as required of a TAVR support guidewire. For example, typically, a support guidewire for use in TAVR has a high stiffness to act as a support wire for over-the-guidewire delivery and deployment of valve components. An example of a guidewire used for TAVR is the Amplatz™ Super Stiff guidewire (Boston Scientific), which has been reported to have a flexural modulus of ~60 GPa (G. Harrison et al., J. Endovasc. Ther. 2011: 18, pp 797-801). Other guidewires used for TAVR include the Confida™ Brecker guidewire (Medtronic Inc.) and Safari™ pre-shaped guidewire (Boston Scientific). The latter are both reported to be stiffer than the Amplatz Super Stiff guidewire, but less stiff than the Lunderquist® Extra-Stiff Wire Guide (Cook Medical) (~158 GPa).

TAVR guidewires are typically available with a standard outer diameter of 0.89 mm (0.035 inch). The sensor guidewire 200 of the first embodiment comprising the tube-in-tube construction as illustrated in FIG. 2, e.g., having an outside diameter of 0.89 mm, can readily accommodate a single FP optical pressure sensor 230 in an inner tube 234 comprising a stainless steel hypotube having an inside diameter of e.g., 0.285 mm to accommodate the optical fiber and optical sensor. The inner tube has an outside diameter (OD) which, together with the outer tubular layer, provides required stiffness characteristics along the length of the sensor guidewire. For example, the inner tubular layer may be a hypotube having an OD in the range from 0.26 to 0.40 mm OD (0.014 to 0.016 inch OD). The flexible tip 206 may have the same diameter as the outer tube 220 of the sensor guidewire or may be tapered to a smaller diameter. For the transfemoral approach, the sensor support guidewire 200 typically has a length in the range of about 260 mm to 300 mm. This length enables over-the-guidewire mounting of a valve delivery device and valve components. For an apical approach, i.e. through a small incision between the ribs, directly into the apex of the left ventricle of the heart, a shorter guidewire and delivery device is typically used. For paediatric use, a sensor support guidewire of smaller dimensions may be used, e.g. a smaller outer diameter, tip size, and smaller spacing of the sensor from the tip. The micro-coil and/or hypotube forming the outer tubular layer is sized to allow for an external coating which provides the sensor guidewire with an appropriate lubricity, e.g. a hydrophilic coating.

The optical fiber 232 extending from the optical sensor along the length of the sensor guidewire 200 is optical coupled through the optical connector 240 to a second length of optical fiber 238 in the flexible optical coupling 208 of the sensor guidewire. The flexible optical coupling 208 provides a flexible optical connection to the input/output connector 212 which connects to the optical input/output port 102-P2 of the controller 100, and it does not require the same stiffness characteristics as the sensor support guidewire 200. For example, the flexible optical connection 208 of the sensor guidewire may simply comprise a length of low cost flexible tubing 222 and a protective outer jacket 223 containing the optical fiber 238. Flexible optical connection 208 has at its proximal end 202 a standard type of optical input/output connector 212, comprising a strain boot 219, for connection of the first optical pressure sensor to a corresponding port 102-P2 of the optical control system. This input/output connector 212 may be a smart connector which has a memory chip or readable tag that stores a sensor ID and calibration data, e.g. a SCAI connector comprising an EEPROM.

Preferably, the optical connector 240 connecting the sensor guidewire 200 to the flexible optical coupling 208 is a separable optical coupler in which the male part of the connector is carried by the proximal end of the sensor guidewire 200, and which has a diameter no greater than a maximum outside diameter $D_g$ (e.g., 0.89 mm) of the external covering of the sensor guidewire 200. Separation of the two parts of the connector 240 enables over-the-wire mounting of a valve delivery system and valve components on the proximal end of the sensor guidewire 200. The female part of the optical connector 240 forms the distal end of the flexible optical connection 208. The body 241 of the female part of the connector 240 may be of sufficient external size to form a handle for manipulating the sensor guidewire 200 to assist with pushing, pulling and twisting the sensor guidewire 200 as the sensor guidewire is inserted and withdrawn. The optical fiber connector 240 comprises alignment means for the optical alignment of ends of the two optical fibers 232 and 238, for example, as illustrated schematically, using a pair of ferrules 243 and an alignment sleeve 242.

FIGS. 3A, 3B and 3C show enlarged axial cross-sectional views of the sensor guidewire assembly illustrated in FIG. 2 taken, respectively, through planes A-A, B-B and C-C of FIG. 2. The cross-section in FIG. 3A through cross-section A-A of the flexible optical connection 208 shows the flexible tubing layer 222 surrounding optical fiber 238, and the outer protective jacket 223. The cross-section in FIG. 3B through cross-section B-B of the TVT sensor support guidewire 200 shows the optical fiber 232 surrounded by protective inner core tube 234 within the outer tube 220. The optical fiber 232 fits slidably within the inner core tube 234. For example, the core tube has an inner diameter of 0.285 mm to accommodate an optical sensor of 0.260 mm diameter, and the optical fiber is a standard optical fiber having an outside diameter in the range from about 0.100 mm to 0.200 mm. The cross-section shown in FIG. 3C taken through cross-section C-C of the distal region of the sensor support guidewire near the sensor shows the sensor 230, the protective inner tube 234 cut away in the sensor region to form a cavity 225 and the surrounding reinforced region 224 of the outer tube 220. An aperture 226 is provided in reinforced region 224 near the sensor 230 to allow for fluid contact with the sensor 230. The outer diameter of the sensor guidewire $D_g$ is indicated in FIGS. 3B and 3C, and, for example, is typically 0.035 inch (0.89 mm) for a guidewire for left heart catheterization. The flexible tubing layers of flexible optical connection 208 shown in FIG. 3A may have any suitable diameter.

Angiographic Sensor Catheter

Figure 4:
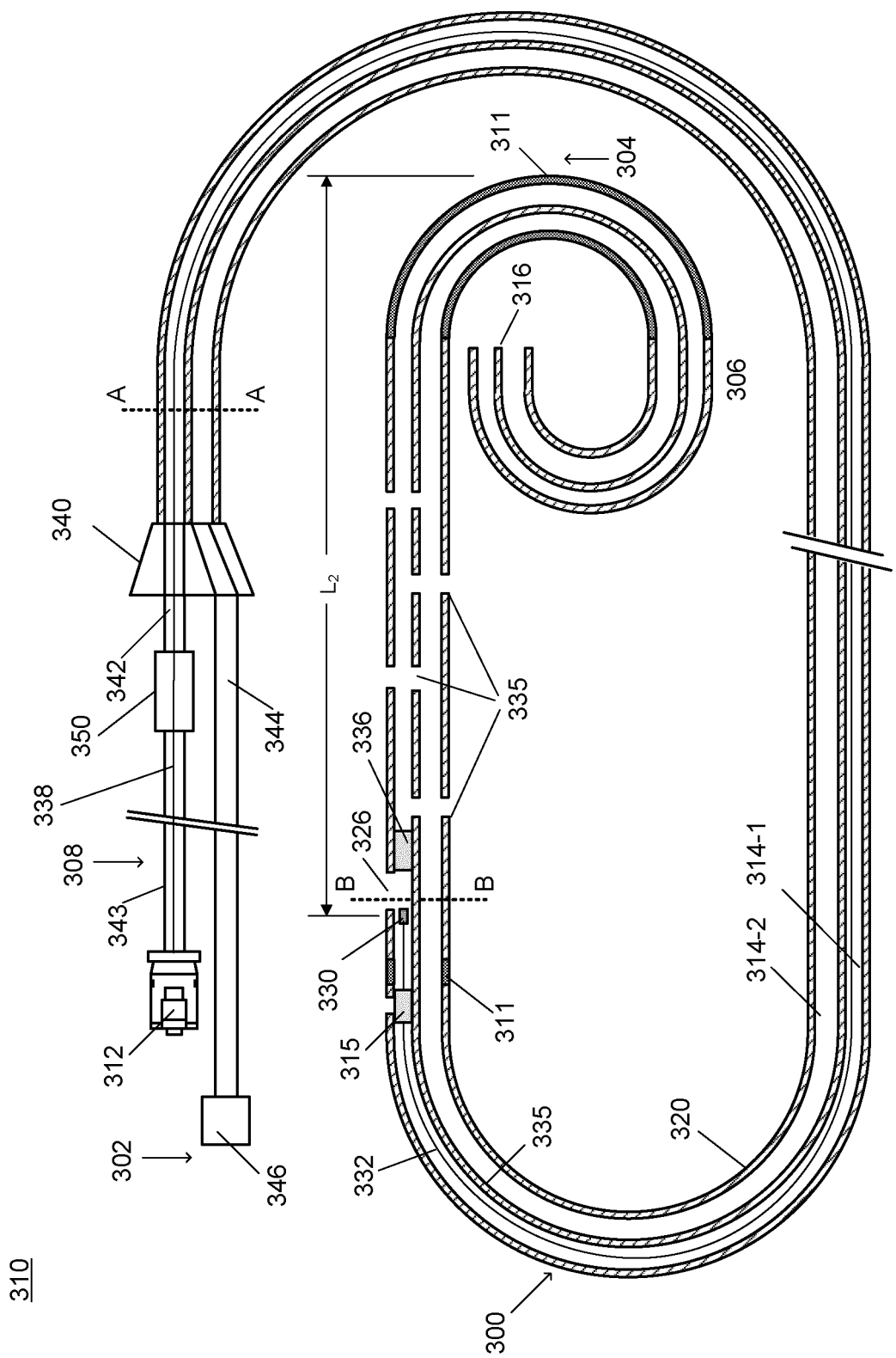
FIG. 4 shows an enlarged schematic longitudinal cross-sectional view of the sensor catheter of the first embodiment, configured for measuring blood pressure in the ascending aorta during TAVR.

An enlarged schematic longitudinal partial cross-sectional view of the assembly 310 comprising a sensor catheter 300 and a flexible optical coupling 308, of the first embodiment, is shown in FIG. 4. The sensor catheter 300 comprises a dual lumen pigtail catheter configured for measuring blood pressure, e.g., in the aorta during TAVR, and for injecting contrast medium, saline or other fluid, e.g., into the LV and the aorta during TAVR. That is, the sensor catheter 300 has the form of a small diameter, angiographic pigtail catheter of the type used to deliver a fluid injection of contrast agent into the aorta near the aortic valve, to allow fluoroscopic imaging of blood flow in the region downstream of the aortic valve and for imaging to look for aortic regurgitation. This type of catheter may be referred to as an angiographic catheter or a diagnostic catheter. However, unlike a conventional pigtail catheter used for injecting contrast medium, the sensor catheter has a first lumen 314-1 containing the optical pressure sensor 330 and optical fiber 332. As illustrated in the longitudinal cross-sectional view shown in FIG. 4, the sensor catheter 300 comprises a length of dual lumen catheter tubing 320, extending from the connection hub 340 to a distal end 304 comprising a pre-formed pigtail tip 306. The first lumen 314-1 accommodates the second optical pressure sensor 330 and its optical fiber 332. The optical pressure sensor 330 is located an appropriate distance L2 from the pigtail tip 306, so that the sensor can be positioned in the ascending aorta when the pigtail tip 306 is positioned close to the cusps of the aortic valve. A sensor aperture 326 for fluid contact is provided in the wall of the first lumen 314-1 near the sensor 330, and the first lumen 314-1 is plugged distally of the sensor position by plug 336. The optical fiber 332 may also be secured in the lumen 314-1 near the sensor 330, e.g. by adhesive 315. A radiopaque marker band 311 is provided near the optical pressure sensor 330, and another radiopaque marker band 311 is also provided at the distal end 304, to assist with positioning the pigtail tip near the aortic valve. The spacing L2 between the sensor 330 and the distal end 304 is selected to place the sensor 330 in the ascending aorta a few centimeters downstream of the aortic valve. The second lumen 314-2 provides for fluid injection and has a plurality of apertures 335 which are spaced around the circumference of the sensor catheter, along a length of the distal region of the sensor catheter near the pigtail distal tip 306, to allow for distributed injection of contrast medium or other fluids. In the distal region beyond the sensor position and the plug 336 in the first lumen, the first and second lumens may be connected to allow for more distributed ejection of fluid through apertures 335. The end 316 of the second lumen 314-2 is open to allow the sensor catheter to be inserted over a guidewire. The connection hub 340 at the proximal end of the sensor catheter has a port for each lumen of the catheter tubing. The port 344 for the second lumen 314-2 for fluid injection comprises a length of flexible tubing 345 extending from the connection hub 340 to a standard type of fluid injection port 346 for coupling to, as example, a syringe. This port also allows for insertion of the sensor catheter into the body over a guidewire. (A conventional port of this type may be referred to as a "tail" of the catheter). The port 342 for the first lumen comprises another length of flexible tubing through which the optical fiber 332 extends to a separable optical connector 350 for detachably connecting the flexible optical coupling 308, which comprises a length of flexible tubing 343 containing an optical fiber 338 and an optical input/output connector 312 for connection to the controller. The separable optical connector 350 is provided near the connection hub 340 to facilitate connection and disconnection of the flexible optical coupling 308, as needed. By way of example, along its length from the connection hub 340 to the pigtail tip 306, the sensor catheter 300 has an outside diameter in the range of about 4 French to 7 French, e.g., 5 French (1.7 mm/0.066 inch).

Figure 5A:
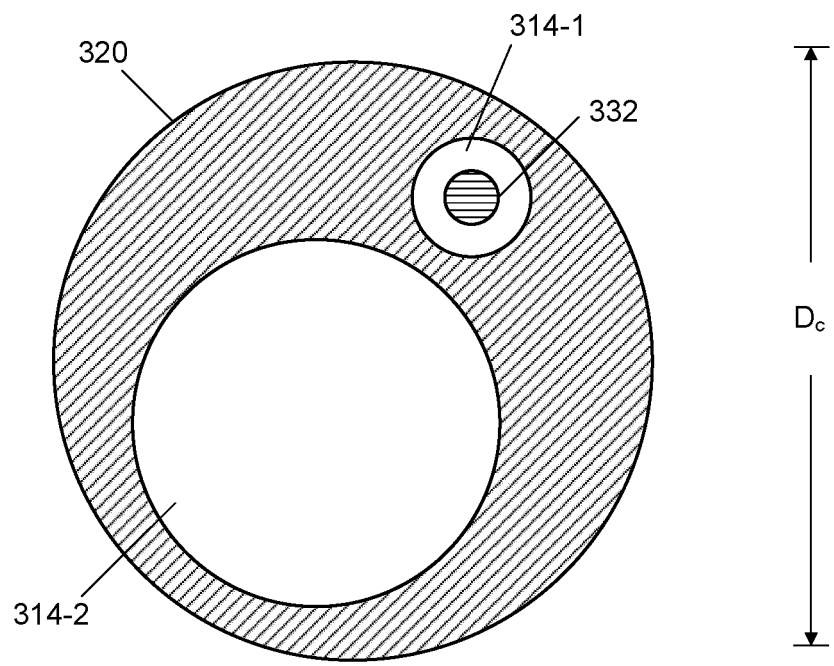
FIGS. 5A and 5B show enlarged axial cross-sectional view of the sensor catheter illustrated in FIG. 4 taken, respectively, through planes A-A and B-B of FIG. 4.
Figure 5B:
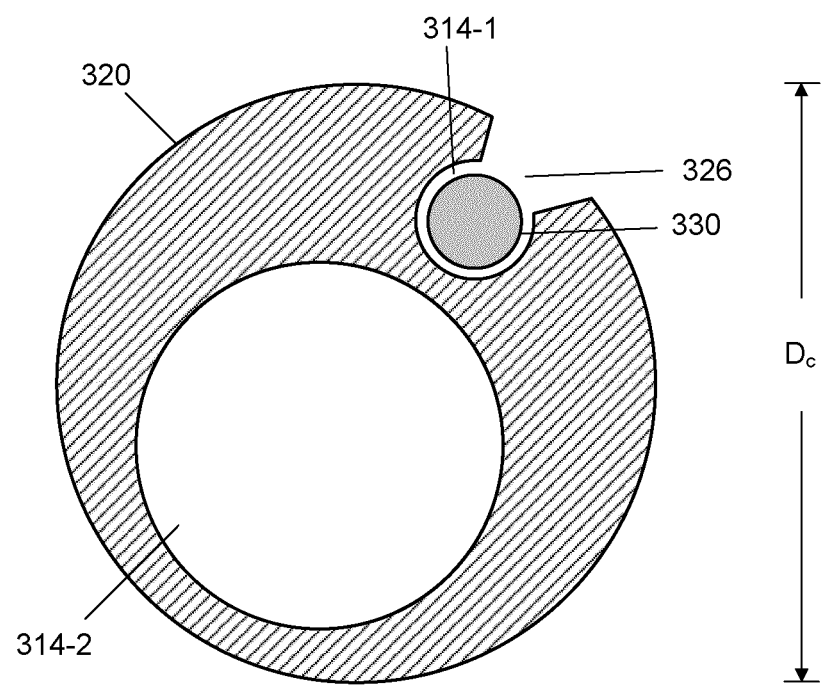

FIGS. 5A and 5B show enlarged axial cross-sectional views of the sensor catheter illustrated in FIG. 4 taken, respectively, through planes A-A and B-B of FIG. 4. The cross-section of FIG. 5A shows lumens 314-1 and 314-2, with optical fiber 332 within the first lumen 314-1. The cross-section of FIG. 5B shows the sensor 330 in lumen 314-1 and aperture 326 adjacent the sensor 330 for fluid contact with the sensor 330. If, for example, the sensor catheter 300 has an outer diameter $D_c$ of 5 French (1.7 mm/0.066 inch), the inner diameter of second lumen 314-2 is sized to be large enough to allow rapid injection of a bolus of contrast medium into the aorta downstream of the aortic valve, e.g. 25 ml to 60 ml of contrast medium over 1 or 2 seconds which requires a larger lumen, e.g. ~1 mm diameter. The inner diameter of the second lumen is also sized to accommodate a conventional guidewire, i.e., for introduction of the sensor catheter into the aorta or other vessel, by passing it over the guidewire. The inner diameter of the first lumen 314-1 is large enough to accommodate the optical fiber 332 and the optical pressure sensor 330, and need not be as large as the fluid injection lumen 314-2. For example, if the sensor 330 has a diameter of 0.260 mm, the first lumen may have a diameter which provides some clearance around the sensor for insertion of the sensor into the lumen, e.g. a lumen of 0.325 mm diameter.

Figure 6A:
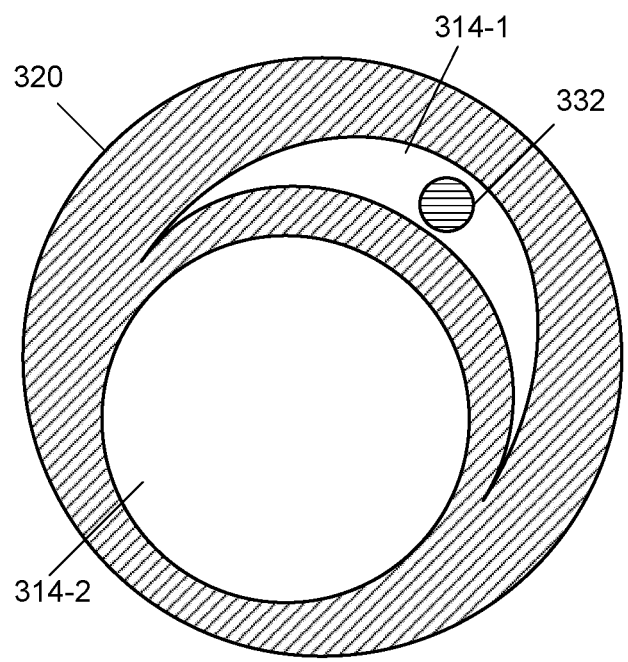
FIGS. 6A and 6B show enlarged axial cross-sectional views through multi-lumen sensor catheters comprising two lumens of alternative embodiments.
Figure 6B:
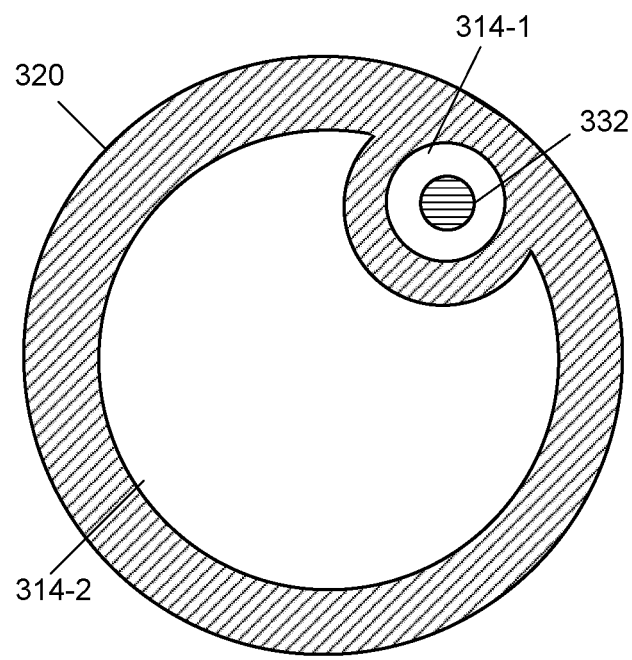

In variants of the dual lumen sensor catheter of the first embodiment illustrated schematically in FIGS. 4, 5A and 5B, the cross-section of the catheter tubing has other geometries or configurations that provide first and second lumens of appropriate sizes. By way of example, cross-sectional views of examples of dual lumen catheters of two alternative embodiments are shown in FIGS. 6A and 6B. Corresponding elements are numbered with the same reference numerals as those shown in FIGS. 4, 5A and 5B. Catheter tubing 320 having a cross-section as shown in FIG. 6A, with first lumen 314-1 for the optical fiber 332 and second lumen 314-2, provides a more uniform wall thickness than the cross-section shown in FIG. 5A, to provide a sensor catheter with more radially symmetric physical characteristics, such as flexibility and torque steering characteristics. Catheter tubing having a cross-section as shown in FIG. 6B provides a similar sized lumen 314-1 for the optical pressure sensor 330 and optical fiber 332 as the sensor catheter cross-section shown in FIG. 5A, and provides a fluid lumen 314-2 with a larger cross-sectional area. Dual lumen sensor catheters having other cross-sections may be used. Also, if required, multi-lumen sensor catheters having one or more additional lumens for other purposes may be used, such as a central lumen for insertion of a guidewire, or additional fluid lumens.

Dual Sensor Support Guidewire for Left Heart Catheterization

Figure 7:
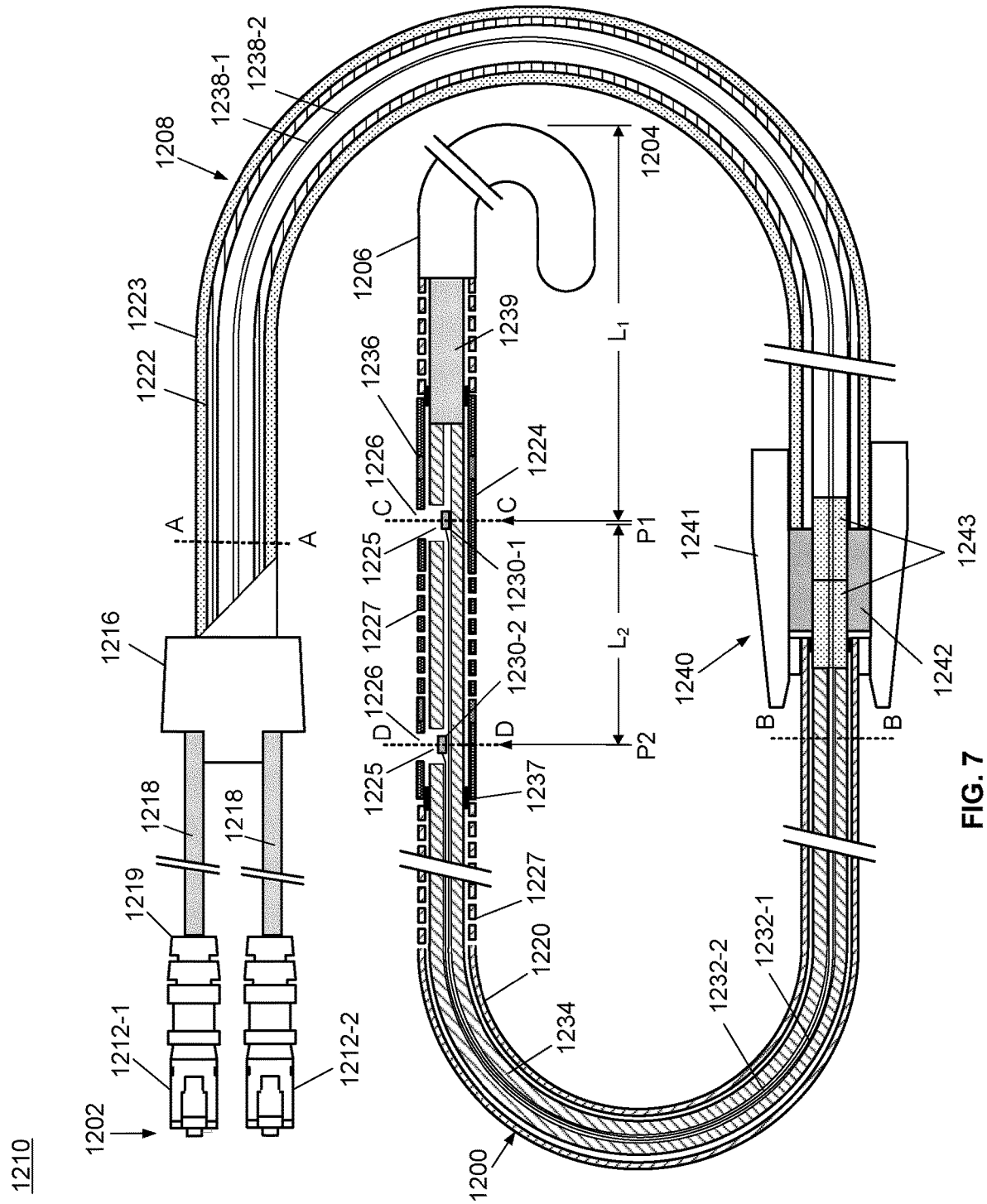
FIG. 7 shows an enlarged schematic longitudinal partial cross-sectional view of a sensor guidewire of a second embodiment, comprising two FP optical pressure sensors configured for diagnostic measurements of blood pressure at two locations, e.g. in the ascending aorta and in the left ventricle (LV) during left heart catheterization.

An enlarged schematic longitudinal partial cross-sectional view of a sensor guidewire assembly 1210 comprising a sensor guidewire 1200 and a flexible optical coupling 1208 of a second embodiment is shown in FIG. 7. The sensor guidewire 1200 of this embodiment comprises two FP optical pressure sensors 1230-1 and 1230-2 and is configured for diagnostic measurements of blood pressure concurrently in two locations, e.g., in the left ventricle (LV) and in the aorta during left heart catheterization. Many parts of this dual sensor guidewire are similar to those of the sensor guidewire 200 of the first embodiment and are labeled with the same reference numerals incremented by 1000. The dual sensor guidewire 1200 extends from the optical coupler 1240 at its proximal end to the atraumatic flexible tip 1206 at the distal end 1204. The dual sensor guidewire is coupled through the separable optical connector 1240 to the flexible optical coupling 1208 for connection by input/output connector 1212 to the controller. The sensor guidewire 1200 comprises a flexible tubular member comprising an outer tubular layer 1220 and an inner tubular layer 1234. Like the sensor guidewire 200 of the first embodiment, the structure and materials of the outer tubular covering 1220 and the inner tubular layer 1234 of the sensor guidewire 1200 are selected to provide stiffness and other required physical characteristics of a support guidewire along its length. For example, most of the length of the flexible tubular covering 1220 of the distal portion of the sensor guidewire 1200 comprises a stainless-steel metal hypotube having an appropriate stiffness/flexibility, while the distal end portion comprises more flexible regions 1227, which comprises a length of flexible stainless-steel micro-coil, and a reinforced, e.g. stiffer, section of hypotube 1224 in between. A first FP optical pressure sensor 1230-1, at position P1, is optically and physically connected to the distal end (i.e. the sensor end) of a first optical fiber 1232-1 which terminates at the proximal end (i.e. connector end) of the sensor guidewire within the optical connector 1240. A second FP optical pressure sensor 1230-2, at position P2, is optically and physically connected to the distal end (i.e. the sensor end) of the optical fiber 1232-2 which terminates at the proximal end of the sensor guidewire within the optical connector 1240. The inner tube 1234 extends around the fibers and extends beyond the sensor end of the fiber 1232-1 towards the tip 1206. In the region of each sensor 1230-1 and 1230-2, there is an aperture 1226 in the outer tubular layer 1220, and the inner tubular layer 1234 is shaped to leave space around the sensor, e.g. cut away to form a cavity 1225, to accommodate the sensor 1230 and to allow for fluid contact with the sensors 1230. As illustrated, the reinforced region 1224 of the outer tube 1220 extends a short length each side of the sensor position P1 and sensor position P2 to provide a required stiffness in the region of the sensors, i.e. where the inner tubular layer 1234 is cut away. A radiopaque marker 1236 may be provided near each sensor, to assist in locating the sensors 1230-1 and 1230-2 in use, e.g. by fluoroscopic imaging. The inner tubular layer 1234 extends a short distance past the first sensor 1230-1 and the tip core wire 1239 forms the core of the flexible tip 1206. To position each sensor 1230 next to its aperture 1226 within the reinforced region 1224 of the outer tubular layer 1220, the inner and outer tubular layers 1220 and 1234 may be secured to each other, e.g. by bonding with adhesive or filler, soldering or welding, at points 1237 at each end of the reinforced region 1224. The atraumatic flexible tip 1206 may be a preformed J-tip, a preformed flat spiral tip, or a preformed 3-dimensional spiral or coiled tip.

Similar to the sensor guidewire 200 of the first embodiment, if the sensor guidewire 1200 is to be used for TVT, e.g. TAVR or TMVR, the sensor guidewire 1200 has physical characteristics along its length, e.g. stiffness, required of a support guidewire to provide a rail for the delivery device and valve components. The optical fibers 1232-1 and 1232-2 in the sensor guidewire 1200 are optically coupled through the dual fiber optical connector 1240 to corresponding optical fibers 1238-1 and 1238-2 in the flexible optical coupling 1208 of the sensor guidewire 1200 to the controller. The dual optical fiber connector 1240 comprises alignment means for optical alignment of the pair of optical fibers 1232-1 and 1232-2 with the pair of optical fibers 1238-1 and 1238-2 using a pair of ferrules 1243 and an alignment sleeve 1242 comprising an alignment facet, e.g., using D-shaped ferrules and a correspondingly shaped alignment sleeve. In use, the sensor guidewire 1200 is connected to a flexible optical connection 1208 to the input/output connectors 1212-1 and 1212-2 which connect to the optical input/output ports 102-P1 and 102-P2 of the controller. For example, the flexible optical connection 1208 for the sensor guidewire 1200 may simply comprise a length of flexible tubing 1222, and protective outer jacket 1223 containing the optical fibers 1238-1 and 1238-2. The flexible optical coupling 1208 of sensor guidewire 1200 differs from that of the sensor guidewire of the first embodiment because it has a connection hub 1216 at its proximal end 1202, which separates the two optical fibers 1238-1 and 1238-2 and provides two separate ports, each comprising a length of flexible tubing 1218 and a standard optical input/output coupler 1212-1, 1212-2, such as a SCAI connector, each comprising a strain boot 1219, for connection of the first optical pressure sensor to a corresponding optical ports 102-P1 and 102-P2 of the controller 100. If required, the optical coupler 1240 connecting the sensor guidewire 1200 and the flexible optical coupling 1208 is a separable optical coupler 1240 in which the male part of the connector is provided by the sensor guidewire 1200 and has a diameter no greater than a maximum outside diameter $D_g$ of the external covering the sensor guidewire 1200. Separation of the two parts of the connector 1240 enables over-the-wire mounting of a valve delivery system and valve components on the sensor guidewire 1200. The female part of the coupler forms the distal end of the flexible optical coupling 1208 to the sensor guidewire 1200. The female part 1241 of the optical connector 1240 may be of sufficient external size to form a handle for manipulating the sensor guidewire, e.g. to assist with pushing and pulling the sensor guidewire 1200 as it is inserted and withdrawn. The flexible optical coupling 1208 of the sensor guidewire may be of a larger diameter, more flexible and fabricated from lower cost components to facilitate fabrication and reduce costs.

Figure 8A:
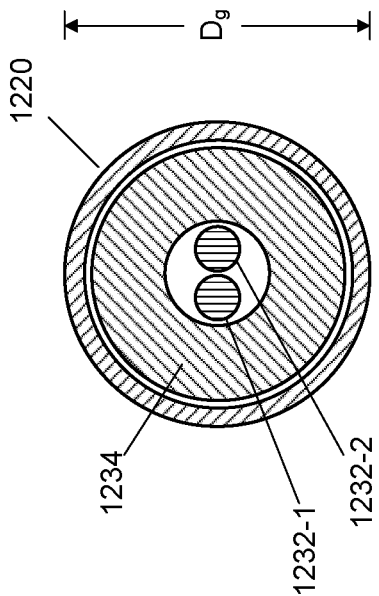
FIGS. 8A, 8B, 8C and 8D show enlarged axial cross-sectional views of the sensor guidewire illustrated in FIG. 7 taken, respectively, through planes A-A, B-B, C-C and D-D of FIG. 7.
Figure 8B:
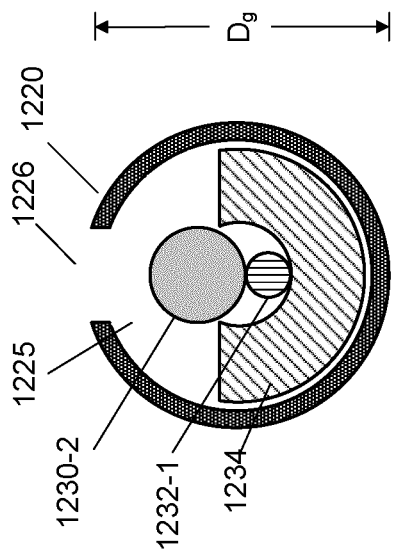
Figure 8C:
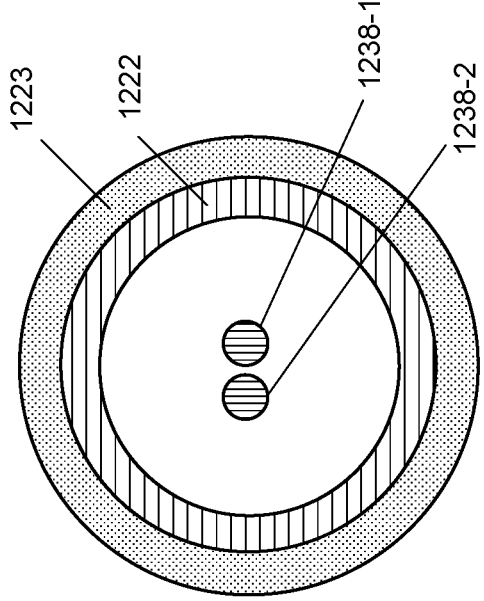
Figure 8D:
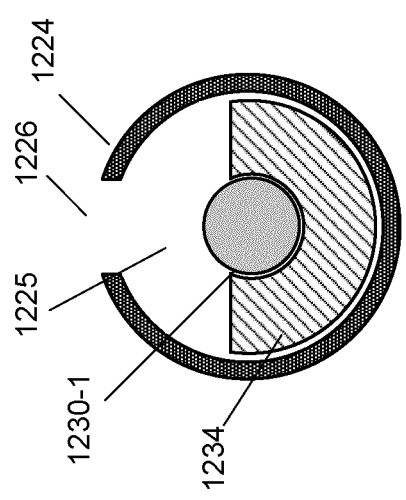

FIGS. 8A, 8B, 8C and 8D show enlarged axial cross-sectional views of the sensor guidewire illustrated in FIG. 7 taken, respectively, through planes A-A, B-B, C-C and D-D of FIG. 7. The cross-section in FIG. 8A through the flexible optical coupling 1208 shows the flexible tubing layer 1222 surrounding optical fibers 1238-1 and 1238-2, and the outer protective jacket 1223. The cross-section in FIG. 8B through the sensor guidewire 1200 shows the optical fibers 1232-1 and 1232-2 surrounded by protective inner tubular layer 1234 within the outer tubular layer 1220. The inner diameter of the inner tubular layer is sized so that the two optical fibers 1232-1 and 1232-2 fit slidably within the inner tubular layer 1234. The cross-section shown in FIG. 8C taken through the distal end of the sensor guidewire 1200 near the first FP optical pressure sensor 1230-1 shows the sensor 1230-1, the protective inner layer 1234 cut away in the sensor region to form a cavity 1225 and the surrounding reinforced region 1224 of the outer tubular layer 1220. An aperture 1226 is provided in reinforced region 1224 near the sensor to allow for fluid contact with the sensor. The cross-section shown in FIG. 8D is taken through the distal end near the second FP optical pressure sensor 1230-2 shows the second FP optical pressure sensor 1230-2 lying beside the first optical fiber 1232-1, where the protective inner layer 1234 is cut away in the sensor region to form a cavity 1225 for the second FP optical pressure sensor 1230-2 and the surrounding reinforced region 1224 of the outer tubular layer 1220. As for the first FP optical pressure sensor 1232-1, an aperture 1226 is provided in a reinforced region 1224 near the second sensor 1230-2 to allow for fluid contact with the second sensor 1230-2. The outer diameter of the sensor guidewire Dg is indicated in FIGS. 3B, 3C, and 3D, and is e.g., typically 0.035 inch (0.89 mm) or less for left heart catheterization. The diameter of the flexible optical coupling 1208 shown in FIG. 8A may have any suitable diameter.

Figure 10A:
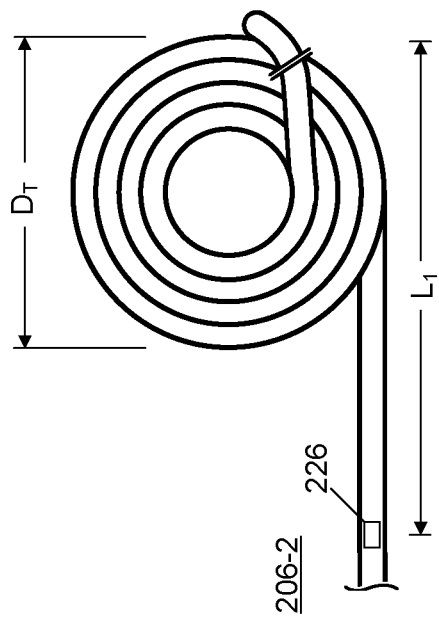
FIGS. 10A and 10B show two schematic side views of a 3-dimensional pre-formed flexible tip of a tapered helical form.
Figure 10B:
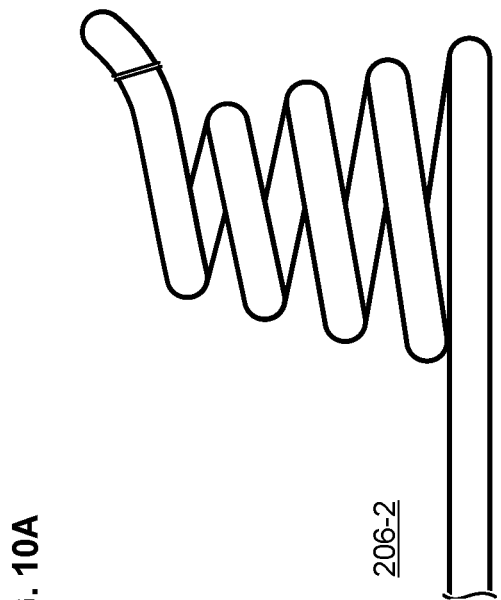
Figure 9A:
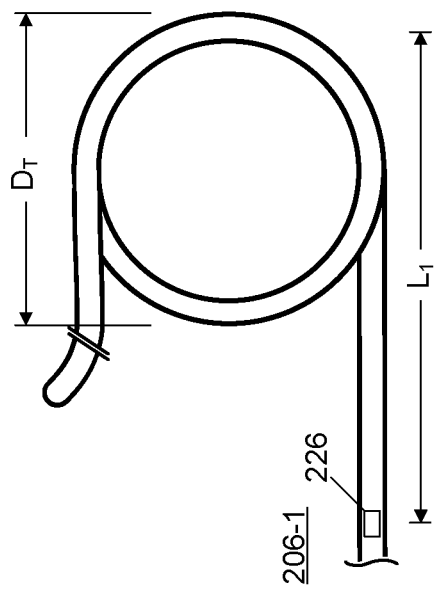
FIGS. 9A and 9B show two schematic side views of a 3-dimensional pre-formed flexible tip of a helical form which may be used with sensor guidewires of the first and second embodiments.
Figure 9B:
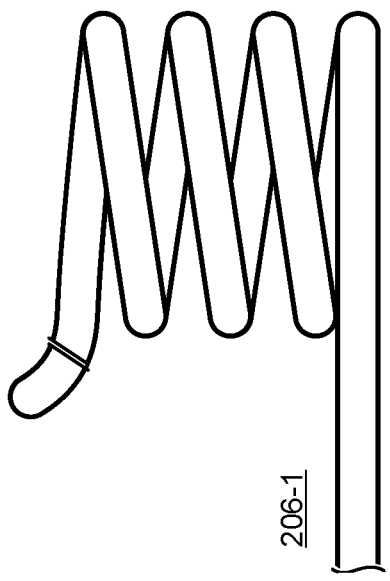

The tip 206 and 1206 of the sensor guidewires 200 and 1200 of the first and second embodiments is preferably an atraumatic pre-formed curved tip such as a pre-formed spiral tip. For example, for firmly anchoring of the tip of the sensor guidewires 200 and 1200 in the left ventricle during TAVR, a 3-dimensional curved spiral tip may be preferred. For example, FIGS. 9A and 9B show two schematic side views of a 3-dimensional pre-formed flexible spiral tip 206-1 having a helical form and comprising an aperture 226 for the FP optical pressure sensor spaced a distance L1 from the apex of the curved tip. Another example of a 3-dimensional pre-formed curved flexible tip 206-2 of a tapered helical form is shown schematically in FIGS. 10A and 10B. The radii, number of turns and other dimensions of the spiral or helix may be selected based on dimensions of the left ventricle. For other TVT procedures, e.g. insertion of a sensor guidewire into other chambers of the heart, e.g. the left atrium, or for an apical approach to the aorta, a flexible preformed curved tip of another form may be used.

Schematic views showing details of components of a TVT sensor support guidewire 2200 of another embodiment are shown in FIGS. 20A to 20E. FIG. 20A shows a schematic partially cut-away view a TVT sensor support guidewire 2200 comprising a main body 2201 having a length L extending between a proximal end 2202 comprising a fiber optic termination 2243 and a sensor region 2203 near the distal end 2204. The distal end comprises a flexible pre-formed curved distal tip 2206. FIG. 20A shows the tapered inner core wire 2239 of the spiral distal tip, with its outer coil removed. The main body 2201 of the TVT sensor support guidewire comprises an inner tubular layer, which may be referred to as a core tube, 2234, extending within an outer tubular layer 2220, e.g., as shown schematically in FIGS. 20D and 20E. In this embodiment the core tube 2234 comprise a stainless steel hypotube. The outer tubular layer 2220 comprises a flexible coilwire 2220-1 covering the core tube 2234 between the fiber optic termination 2243 and the sensor region 2203 of the sensor guidewire, and a length of stainless steel hypotube 2220-2 in the sensor region 2203 (FIG. 20B). As shown in more detail in the enlarged view in FIG. 20B, the hypotube 2220-2 provides reinforcement and stiffness to the outer tubular layer in the sensor region 2203 around the sensor aperture 2226. An enlarged view of the proximal end 2202 of the sensor guidewire is shown in FIG. 20C, showing the fiber optic termination comprising an optical input/output micro-connector 2212, e.g. a ceramic ferrule 2243 surrounding the connector end of the optical fiber 2232, and an outer sleeve 2245. The outer sleeve 2245, e.g. a length of stainless steel hypotube, extends a short distance between the ferrule 2243 and the flexible coil wire 2220-1 to reinforce and stiffen the proximal end of the sensor guidewire near the ferrule 2243. The ferrule 2243 is configured to insert into a corresponding female part of an optical connector carried by a flexible optical coupling, such as a length of optical cable, for connecting the sensor guidewire 1200 to the optical controller 100, as illustrated for example in FIG. 1, for sensor guidewire 200 of the first embodiment. Preferably, the ferrule 2243 and the outer sleeve 2245 have a maximum outer diameter similar to the maximum diameter of the main body 2201 of the sensor guidewire, e.g., 0.035 inch, to allow for over-the-wire mounting of the components for TVT, such as a catheter carrying a valve delivery device. An enlarged view of part of the sensor guidewire in the sensor region 2203 is shown in FIG. 20D, with the outer tubular layer comprising the hypotube 2220-2 removed to show the inner core tube 2234 comprising aperture 2226 near the FP optical pressure sensor 2230, and the core wire 2239 which forms the core of the spiral tip 2206 (FIG. 20A). A cross-sectional view of the sensor region is shown in FIG. 20E to show details of the inner core tube 2234 and the outer sensor hypotube 2220-1 near the sensor 2230. In this embodiment, inner core tube 2234 is cut away to form an aperture 2228 in the region where the sensor 2230 is placed and the sensor aperture or "pressure window" 2226 in the outer hypotube 2220-2 is formed by a through hole which is drilled right through the sensor hypotube 2220-2 in the sensor region, to provide an aperture on each side of the sensor position.

Control System

Referring to the controller 100 shown schematically in FIG. 1, the controller of the dual sensor system may be used with a sensor guidewire and a sensor catheter for concurrent blood pressure measurements at two locations. Alternatively, the same controller may be used with a dual sensor guidewire such as described with reference to FIG. 7.

For dual optical pressure sensors, the controller 100 has a corresponding number of signal processing channels with optical ports 102-P1 and 102-P2 for optical connectors each of the optical pressure sensors as illustrated schematically in FIG. 11A. Each channel comprises an optical control unit, which may be referred to as a signal conditioner, comprising an optical light source and detector for operating a FP optical pressure sensor, associated signal processing electronics and communications interfaces providing digital ports 132, and analog ports 134 for input/output signals to connectors for an ANSI BP-22 compliant PCM. For example, as illustrated schematically in the block diagram in FIG. 11B, each channel of the control system comprises a signal conditioner 110, that comprises the light source and detector and an optical interface 112 for coupling, via respective input/output ports, to an optical fiber and FP optical pressure sensor of a sensor catheter or a sensor guidewire. Calibration data from the sensor EEPROM is input at interface 114 to digital interface 116 which provides calibration data to the signal conditioner 110. The control system also comprises processing means and data storage, e.g. a microprocessor 120, and associated firmware 122, RAM 124, display and indicators 126. The signal conditioner 110 comprises hardware and software configured for processing optical data indicative of pressure values to output calibrated digital sensor data to the microprocessor 120. Digital outputs from the microprocessor 120 are provided to the digital interface 128 comprising standard digital ports 132 and to BP-22 signal converter 130 which provides analog ports 134 for input/output signals for a BP-22 compliant patient care monitor (PCM). The system also comprises AC/DC power electronics 125 for these components.

Where the controller is to be interfaced to a BP-22 compliant PCM for monitoring blood pressure data, and the PCM is configured for displaying blood pressure waveforms, i.e. a pressure waveform from each optical pressure sensor, on a graphical user interface, the concurrent blood pressure waveforms for each of the FP optical pressure sensors may be displayed for one or more time intervals, and during one or more cardiac cycles. The PCM may be further configured to derive hemodynamic parameters from the blood pressure data and display numeric values of the parameters, such as aortic regurgitation index, as well as display the pressure waveforms from each sensor.

If the controller is not connected to a BP-22 compliant patient monitor, digital outputs may be provided to a digital patient monitoring system or to a general-purpose computer 500, such as a tablet PC, running software configured to display of the pressure waveforms and associated hemodynamic parameters. Alternatively, the microprocessor 120 of the controller 100 may be configured to generate digital outputs for displaying of blood pressure waveforms and other hemodynamic parameters on a monitor linked directly to the controller 100.

The user interface of the PC or PCM may allow the operator to input user data such as patient identification, and data interfaces may be provided to output data to other devices or systems, or receive data from other sources, such as from other sensors or monitoring systems, which are typically used in an ICU or OR. For example, in a cardiac catheterization laboratory, the control system 100 for a sensor catheter and sensor guidewire may be coupled to, or part of, a computing system controlling other equipment, and which is equipped with one or more large screen displays close to the operating table, and other remote displays in a monitoring area. The latter are used to display various forms of data, sequentially, concurrently, or on demand. Such data may include, e.g. fluoroscopic imaging, with or without contrast media, and transesophageal echocardiography (TEE) images, as well as sensor data comprising pressure waveforms from the sensor catheter and sensor guidewire and associated hemodynamic parameters calculated or derived from the received FP optical pressure sensor data.

In practice, pressure waveforms and pressure values vary from patient to patient and may be dependent on a number of factors, such as, whether or not the patient has a healthy or diseased heart, or other conditions that may affect functioning of the heart. Skilled medical practitioners will recognize characteristic variations in each pressure waveform and associated pressure values, indicative of e.g. valvular stenosis or other patient physiology. For example, in use of dual sensor system comprising a sensor catheter and a sensor guidewire, concurrent pressure measurements from two FP optical pressure sensors enable the cardiologist to directly compare pressure waveforms and hemodynamic parameters, in real-time, to assess functioning of the heart valve. For example, the aortic regurgitation index (ARi) is an important parameter for assessing functioning of the aortic valve. The ARi is computed from measured values of the left ventricular end-diastolic pressure (LVEDP), diastolic blood pressure (DBP), and systolic blood pressure (SBP), which is defined as:

ARi=((DBP−LVEDP)/SBP)×100

Examples: Use of Dual Sensor System for TAVR and TMVR

Figure 12:
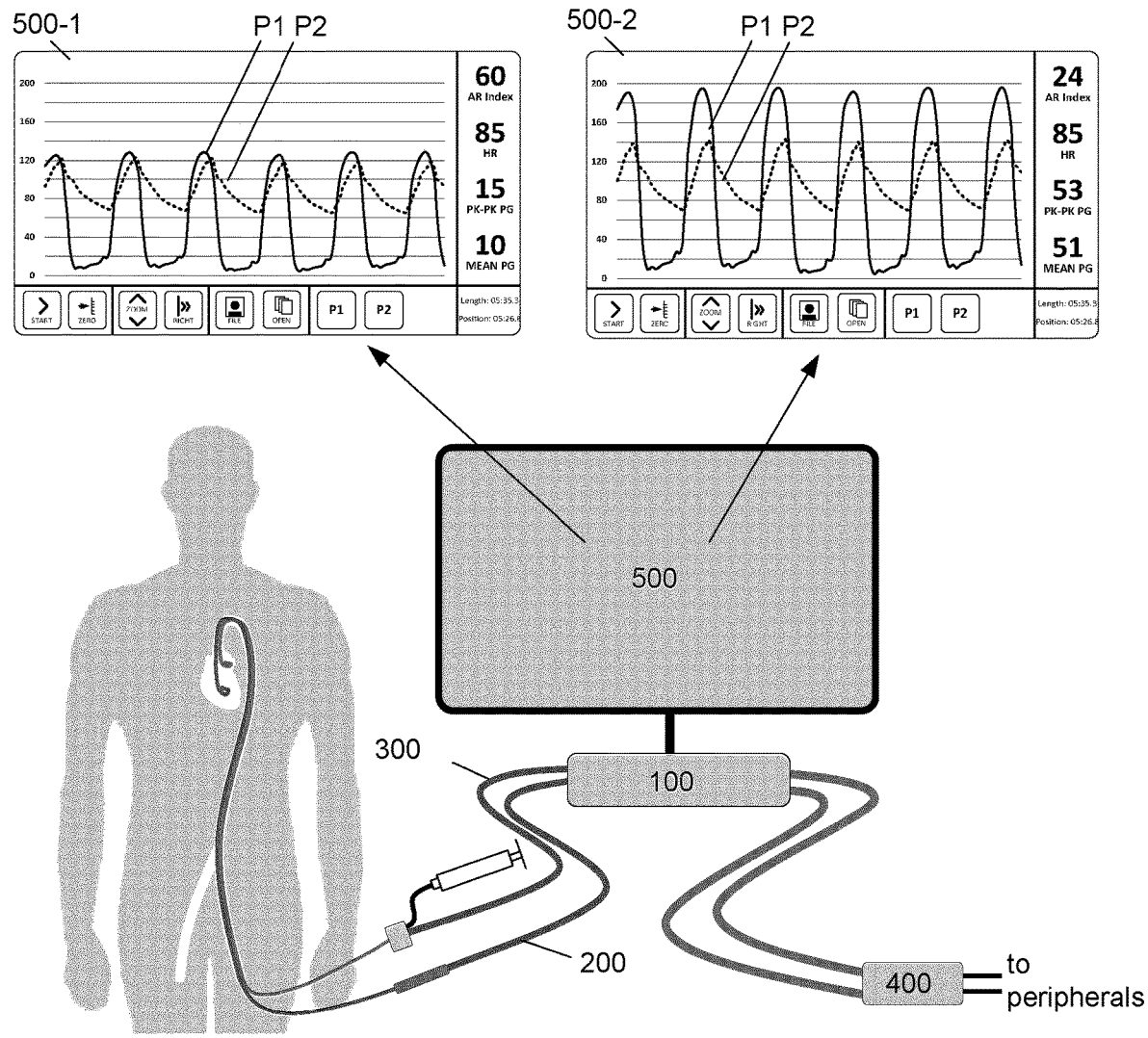
FIG. 12 shows a schematic diagram to illustrate deployment of a dual sensor system of the first embodiment for measurement of pressure in the ascending aorta (Ao) and the left ventricle (LV) in which the user interface is displaying pressure waveforms and hemodynamic parameters including an aortic regurgitation index (ARi) indicative of a) a healthy heart and b) a heart with significant aortic regurgitation.

FIG. 12 shows a schematic diagram to illustrate deployment of a dual sensor system of the first embodiment comprising a sensor catheter 300 for measurement of pressure in the ascending aorta (Ao) and a sensor guidewire 200 for concurrent measurement of pressure in the left ventricle (LV), and in which the controller 100 is connected to a dedicated user interface, e.g. a tablet PC 500, for displaying pressure waveforms and associated hemodynamic parameters including an aortic regurgitation index (ARi). FIG. 12 includes schematic examples of screen shots indicative of a) a healthy heart, as represented by screenshot 500-1 and b) a heart with significant aortic regurgitation, as represented by screenshot 500-2. In this example, the calibrated pressure data is also output via analog ports of controller 100 to a BP-22 PCM 400, e.g. for further processing or display of data by other equipment, such as the large screen monitors, as typically used in a Cath Lab.

Figure 13:
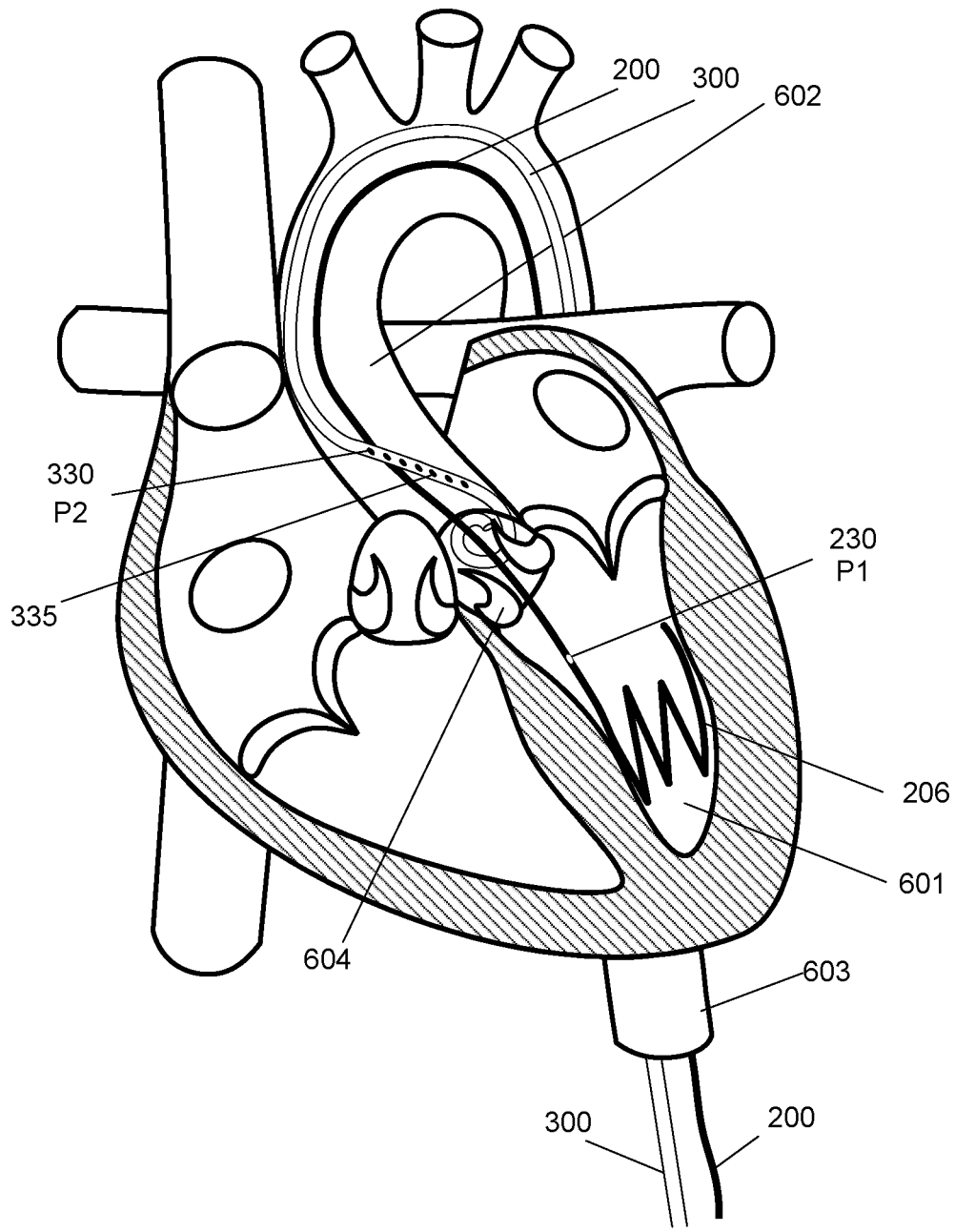
FIG. 13 shows a schematic partial cross-sectional diagram of a human heart to illustrate placement of the sensor catheter and sensor support guidewire of the dual sensor system of the first embodiment for diagnostic measurements of hemodynamic parameters, wherein the sensor guidewire is positioned for continuous blood pressure measurement within the left ventricle (LV) and the sensor catheter is positioned for concurrent and continuous measurement of blood pressure within the ascending aorta.

A schematic partial cross-sectional diagram of a human heart 600-1 is shown in FIG. 13 to illustrate placement of the sensor catheter 300 and sensor support guidewire 200 of the dual sensor system of the first embodiment for diagnostic measurements of hemodynamic parameters. The distal region of sensor support guidewire 200 is positioned for continuous blood pressure measurement by FP optical pressure sensor 230 (P1) within the left ventricle (LV) 601. The sensor catheter 300 is positioned for concurrent and continuous measurement of blood pressure by sensor 330 (P2) positioned within the ascending aorta 602, downstream of the aortic valve 604, i.e. with the pigtail of the sensor catheter 300 positioned close to the cusps of the aortic valve 604, and apertures 335 arranged for injection of contrast medium into the ascending aorta 602 downstream of the aortic valve 604. The sensor catheter 300 replaces a conventional pigtail catheter that is in place for contrast medium injection during TAVR and preferably has the same outer diameter, and other physical characteristics, of a conventional pigtail catheter of this type, so it may be used interchangeably without change of procedure, other than connecting the optical connector directly or indirectly to the control unit (e.g. control unit 100 shown in FIG. 1) when activation of the FP optical pressure sensor 330 P2 for pressure measurements is required. The tip 206 of the sensor support guidewire 200 is introduced through the descending aorta 603, the ascending aorta 602 and through aortic valve 604 in the manner of a conventional support guidewire for TAVR. The preformed curved tip 206 anchors the sensor guidewire in the left ventricle 601 and positions the sensor 230 within the left ventricle, upstream of the aortic valve 604, as illustrated schematically. Thus, the FP optical pressure sensors 230 (P1) and 330 (P2) are positioned so that one sensor is located upstream of the aortic valve and one sensor located downstream of the aortic valve. This arrangement enables concurrent blood pressure measurements in the ascending aorta and in the left ventricle, e.g., for measurement of a transvalvular pressure gradient across the aortic valve and other hemodynamic parameters. In use of a dual sensor system comprising a sensor guidewire and a sensor catheter as illustrated schematically in FIG. 13, which are independently movable, the relative positions of the two sensors 230 and 330 may be adjusted to some extent, depending on a patient's size and individual anatomy.

Figure 14:
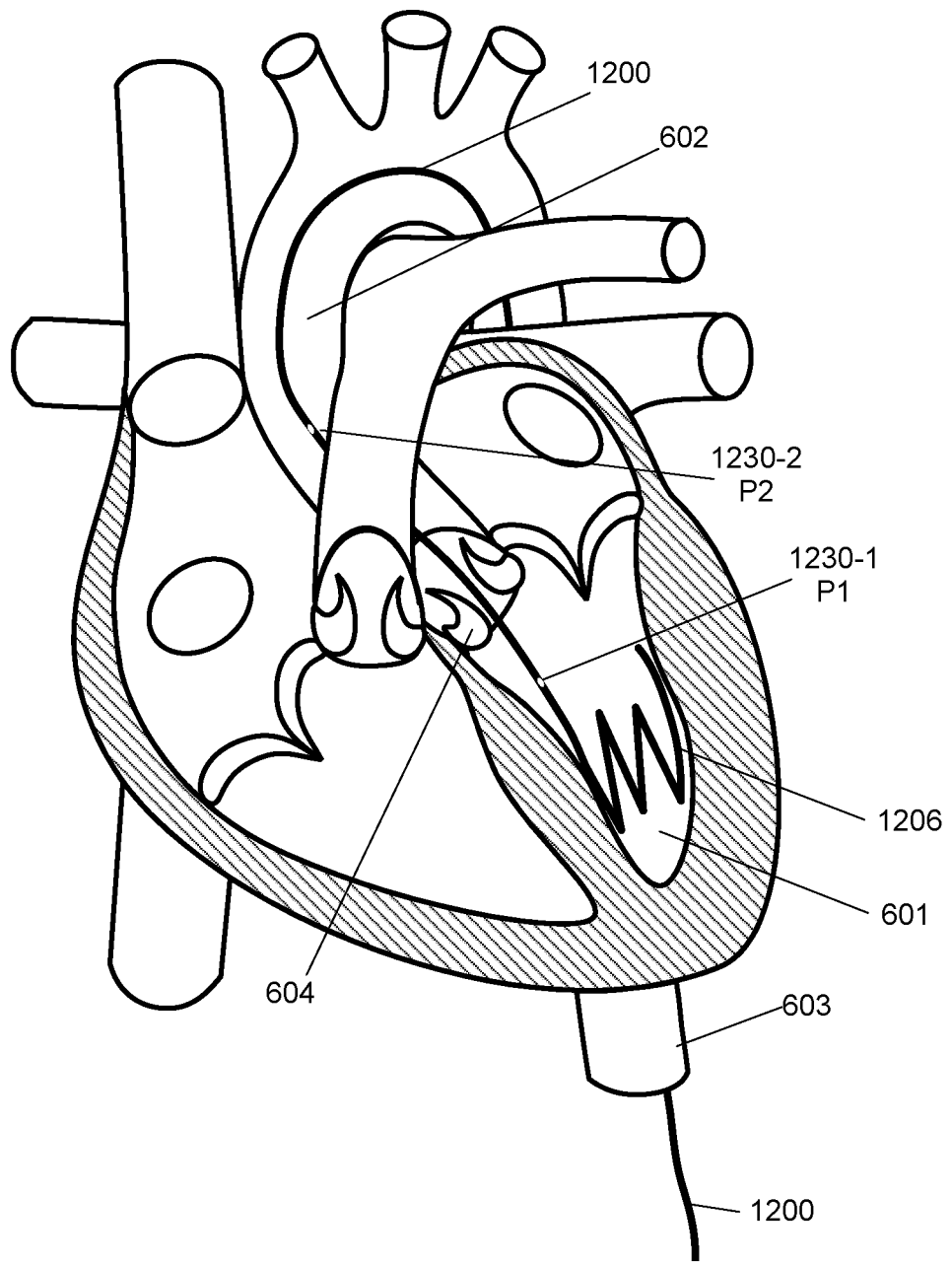
FIG. 14 shows a schematic partial cross-sectional diagram of a human heart to illustrate placement of the dual sensor support guidewire of the second embodiment for diagnostic measurements of hemodynamic parameters, wherein the sensor support guidewire is positioned for continuous blood pressure measurement within the left ventricle (LV) and for concurrent and continuous measurement of blood pressure within the ascending aorta (e.g., transfemoral approach)

A schematic partial cross-sectional diagram of a human heart 600-2 is shown in FIG. 14 to illustrate placement of the dual sensor guidewire 1200 of the second embodiment for diagnostic measurements of hemodynamic parameters within the left heart. The tip 1206 of the sensor support guidewire 1200 is introduced through the descending aorta 603, the ascending aorta 602 and through aortic valve 604 in the manner of a conventional support guidewire for TAVR. As illustrated schematically the helical spiral tip 1206 anchors the sensor guidewire in the left ventricle 601, with the first optical pressure sensor 1230-1 (P1) located within the left ventricle 601. The second optical pressure sensor 1230-2 (P2) is positioned in the ascending aorta 602. For example, a sensor spacing of about 20 mm to 50 mm would be sufficient to place one sensor upstream and one downstream of a heart valve. However, blood pressure measurements may be affected by significant turbulence in the blood flow through the cardiac cycle. For this reason, a larger spacing, e.g. 70 mm to 100 mm, between the two sensor locations may be preferred to enable one sensor to be located further into the left ventricle 601 and another sensor to be located further upstream of the aortic valve 604 in the aorta 602, so that both sensors are located in regions of less turbulent flow, i.e. spaced some distance each side of the aortic valve 604. For example, based on review of CT scans to assess dimensions of the heart of a number of subjects, an 80 mm spacing of two pressure sensors may typically be required, e.g., to enable measurement of a transvalvular pressure gradient. For paediatric use, a smaller gauge sensor guidewire and closer spacing of the sensors may be appropriate.

Figure 15:
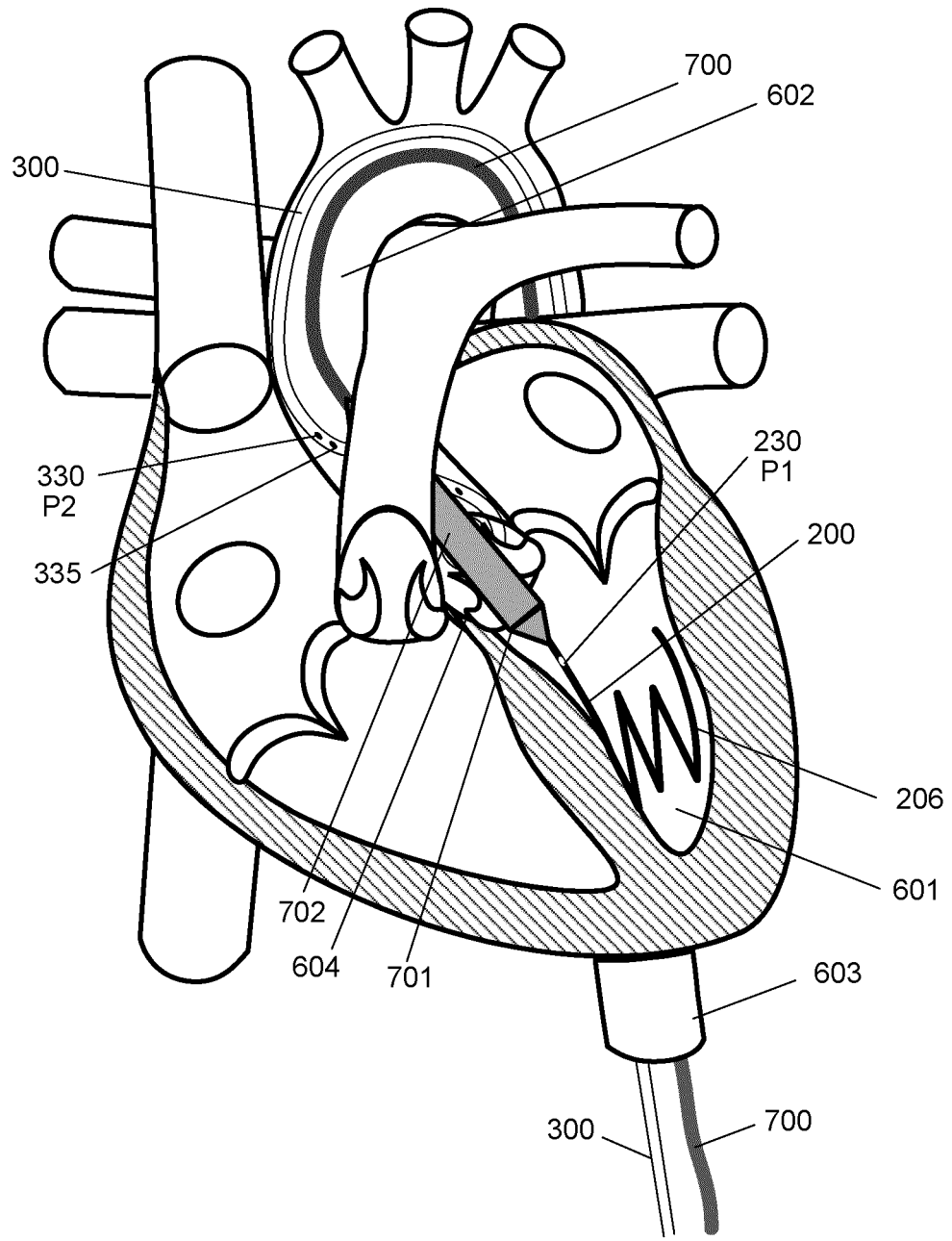
FIG. 15 shows a schematic partial cross-sectional diagram of a human heart to illustrate placement of the sensor catheter and sensor guidewire of the dual sensor system of the first embodiment for measurements of hemodynamic parameters, including concurrent measurements of blood pressure in the LV and ascending aorta during TAVR (e.g., trans-femoral approach)

A schematic partial cross-sectional diagram of a human heart 600-3 is shown in FIG. 15 to illustrate placement of the sensor catheter 300 and sensor guidewire 200 of the dual system, for measurements of hemodynamic parameters, including concurrent measurements of blood pressure in the ascending aorta and LV during TAVR. The tip 206 of the sensor support guidewire 200 is introduced through the descending aorta 603, the ascending aorta 602 and through aortic valve 604. In this example, the distal region of the sensor catheter 300 is positioned with sensor 330 (P2) in the aorta 602 and the distal region of the sensor guidewire 200 is positioned with the sensor 230 (P1) in the left ventricle 601, similar to the arrangement shown in FIG. 13. Apertures 335 in the sensor catheter provide for injection of contrast medium into the ascending aorta. A catheter 700 carrying a valve delivery device 702 is mounted over the sensor guidewire 200, and is shown with the nose cone 701 of the valve delivery device 702 positioned through the aortic valve 604 ready for deployment of a prosthetic aortic valve. Even when the valve delivery device is this position during valve deployment, the first optical pressure sensor 230 (P1) of the sensor support guidewire is positioned to enable continuous measurement of the LV pressure and the second optical pressure sensor 330 (P2) of the sensor catheter is positioned to enable continuous measurement of the Aortic pressure. Since the catheter 700 of the valve delivery device 702 is mounted over the sensor guidewire 200 in the aorta, if the sensor guidewire 200 is provided with an optional second sensor as shown in FIG. 14, the second sensor in the aorta would be covered by the catheter 700 at this stage in valve deployment. During this time, the optional second sensor of the sensor guidewire would be blocked or disabled from measuring blood pressure in the aorta. This application of the dual sensor system comprising a sensor guidewire 200 and a sensor catheter 300 enables pressure measurements in the left ventricle and in the ascending aorta be monitored on demand during TAVR, and potentially continuously, before, during and after valve deployment.

In this disclosure, enabling "continuous" measurements of blood pressure refers to enabling "on demand" sampling of blood pressure measurements at any time during a TVT procedure. A typical heart rate is e.g., 60 to 120 beats per minute. Typically, the digital signal conditioner for the first and second FP optical pressure sensors use a much faster sampling rate, e.g., 250 Hz, to generate digital pressure waveforms for blood pressures for LV and Ao. These digital pressure waveforms, and derived parameters, may be output to a digital monitor for display and further analysis. To enable interfacing to a BP-22 compliant PCM, the control unit comprises a signal converter that converts the digital waveforms and generates analog input and output signals for interfacing to a BP-22 compliant PCM.

FIGS. 13 to 15 show examples of an aortic approach to the left ventricle 601, which is the most commonly used approach for TAVR e.g. using either transfemoral or transradial percutaneous entry for left heart catheterization. Alternatively, in some patients, an apical approach for TAVR may be used (not shown in the drawings), where a small incision is made between the ribs to allow the sensor guidewire and valve delivery device to be inserted into the heart through the apex of the left ventricle. Since the latter is a more direct approach, a shorter sensor guidewire and valve delivery device may be used; the length, diameter, stiffness and other characteristics of the sensor guidewire are therefore selected accordingly.

Figure 16:
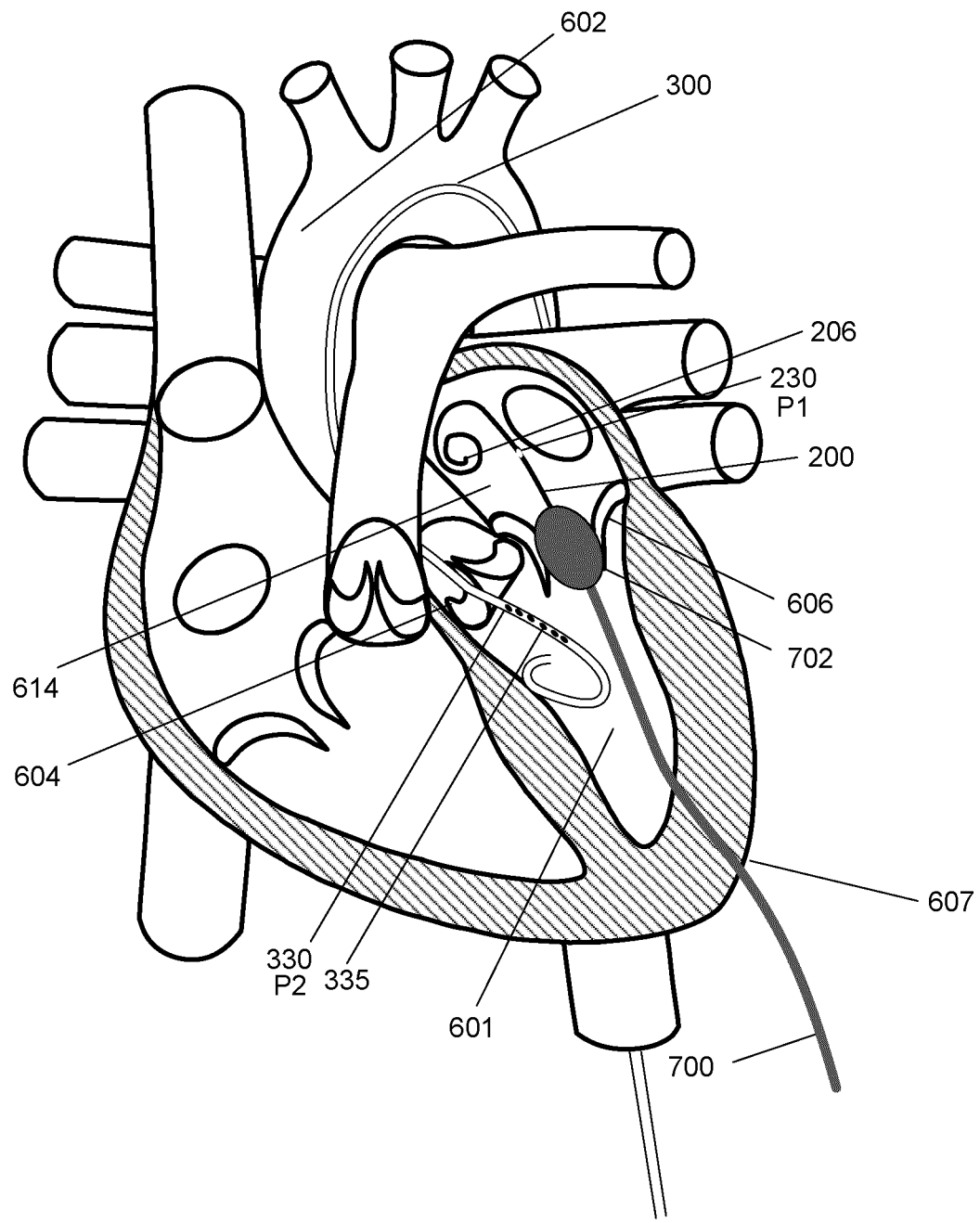
FIG. 16 shows a schematic partial cross-sectional diagram of a human heart to illustrate placement of the sensor catheter and sensor guidewire of the dual sensor system of the first embodiment for measurements of hemodynamic parameters, including concurrent measurements of blood pressure in the LV and RA during TMVR, in which the sensor guidewire passes through the apex of the heart (apical approach)

An example of an apical approach to the left ventricle 601, i.e. through apex 607 of the left ventricle 601, to access the mitral valve 606 for TMVR is shown in FIG. 16, which shows a schematic partial cross-sectional diagram 600-4 of a human heart to illustrate placement of the sensor catheter 300 and sensor guidewire 200 of dual sensor system, for measurements of hemodynamic parameters, including concurrent measurements of blood pressure in the LV 601 and left atrium (LA) 614 during TMVR. As illustrated schematically in FIG. 16, in this example, the tip 206 of sensor guidewire 200 is introduced through the apex 607 of the LV 601 and passed through the mitral valve 606 into the LA 614, for measurement of LA pressure by pressure sensor 230 (P1) positioned in the LA. The sensor catheter 300 is inserted through the descending aorta into the ascending aorta 602, and the tip of the catheter is advanced through the aortic valve 604 into the LV 601 for injection of contrast medium into the LV 601 through apertures 335, and for measurement of LV pressure by pressure sensor 330 (P2). A catheter 700 carrying mitral valve delivery device 702 is delivered over the sensor support guidewire 200 and positioned through the mitral valve 606. This arrangement allows for blood pressure monitoring in the LV and LA during TMVR.

Figure 17:
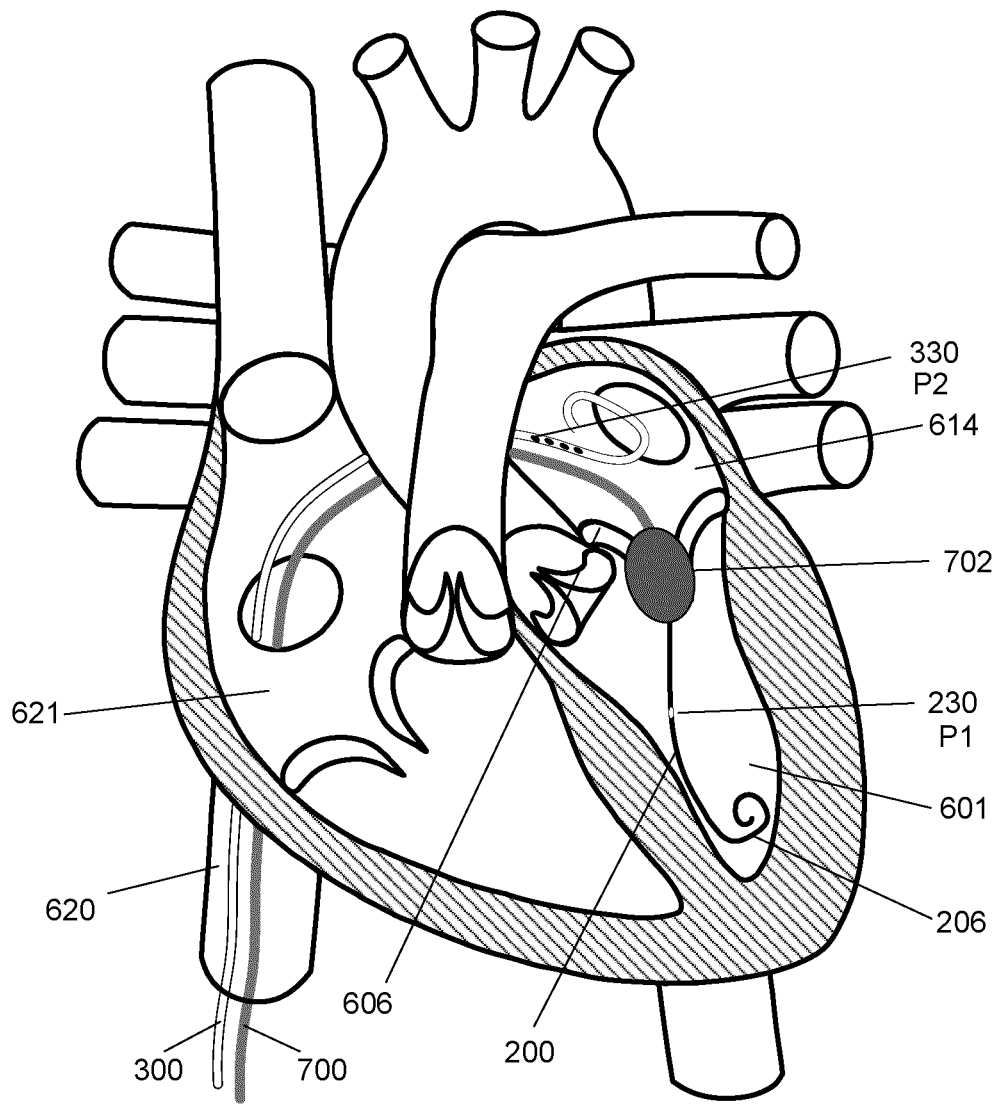
FIG. 17 shows a schematic partial cross-sectional diagram of a human heart to illustrate placement of the sensor catheter and sensor guidewire of the dual sensor system of the first embodiment for measurements of hemodynamic parameters, including concurrent measurements of blood pressure in the LV and RA during TMVR (trans-septal approach)

For comparison, a schematic partial cross-sectional diagram 600-5 is shown in FIG. 17 to illustrate placement of the sensor catheter 300 and sensor guidewire 200 using a trans-septal approach, via the inferior vena cava 620 and the right atrium 621, via a trans-septal puncture to enter the LA 614 and LV 601 for TMVR. In this example, the tip of the sensor catheter 300 is positioned in the LA 614 for measurement of LA pressure by pressure sensor 330 (P2). The tip 206 of the sensor guidewire 200 is positioned in the LV 601 for measurement of LV pressure by pressure sensor 230 (P1). Catheter 700 carrying valve delivery device 702 is delivered over the sensor support guidewire 200 to position the valve delivery device through the mitral valve 606.

Figure 18:
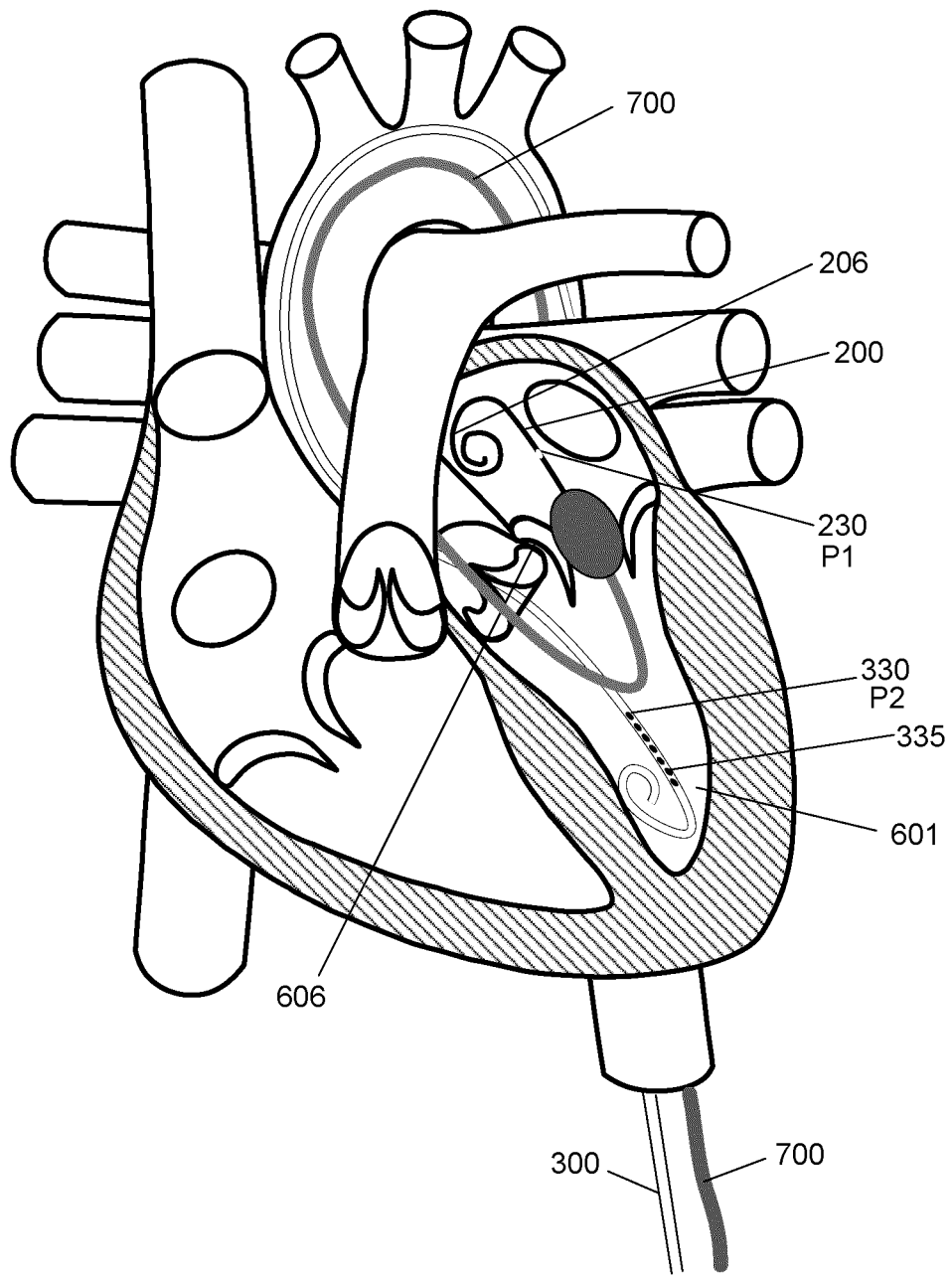
FIG. 18 shows a schematic partial cross-sectional diagram of a human heart to illustrate placement of the sensor catheter and sensor guidewire of the dual sensor system of the first embodiment for measurements of hemodynamic parameters, including concurrent measurements of blood pressure in the LV and RA during TMVR (e.g. transfemoral approach)

A schematic partial cross-sectional diagram 600-6 is shown in FIG. 18 to illustrate placement of the sensor catheter 300 and sensor guidewire 200 of the dual sensor system using an aortic approach to the LV and LA for TMVR. The tip 206 of the sensor guidewire 200 is inserted through the aorta, through the aortic valve into the LV 601 and then advanced through the mitral valve 606 into the LA to position pressure sensor 230 (PA) in the LA for measurement of LA pressure. The sensor catheter 300 is introduced through the aorta, and through the aortic valve for measurement of LV pressure by pressure sensor 330 (P2), and injection of contrast medium through apertures 335. The catheter 700 carrying the valve delivery device 702 is inserted over the sensor support guidewire 200 to position the valve delivery device through the mitral valve 606.

Figure 19:
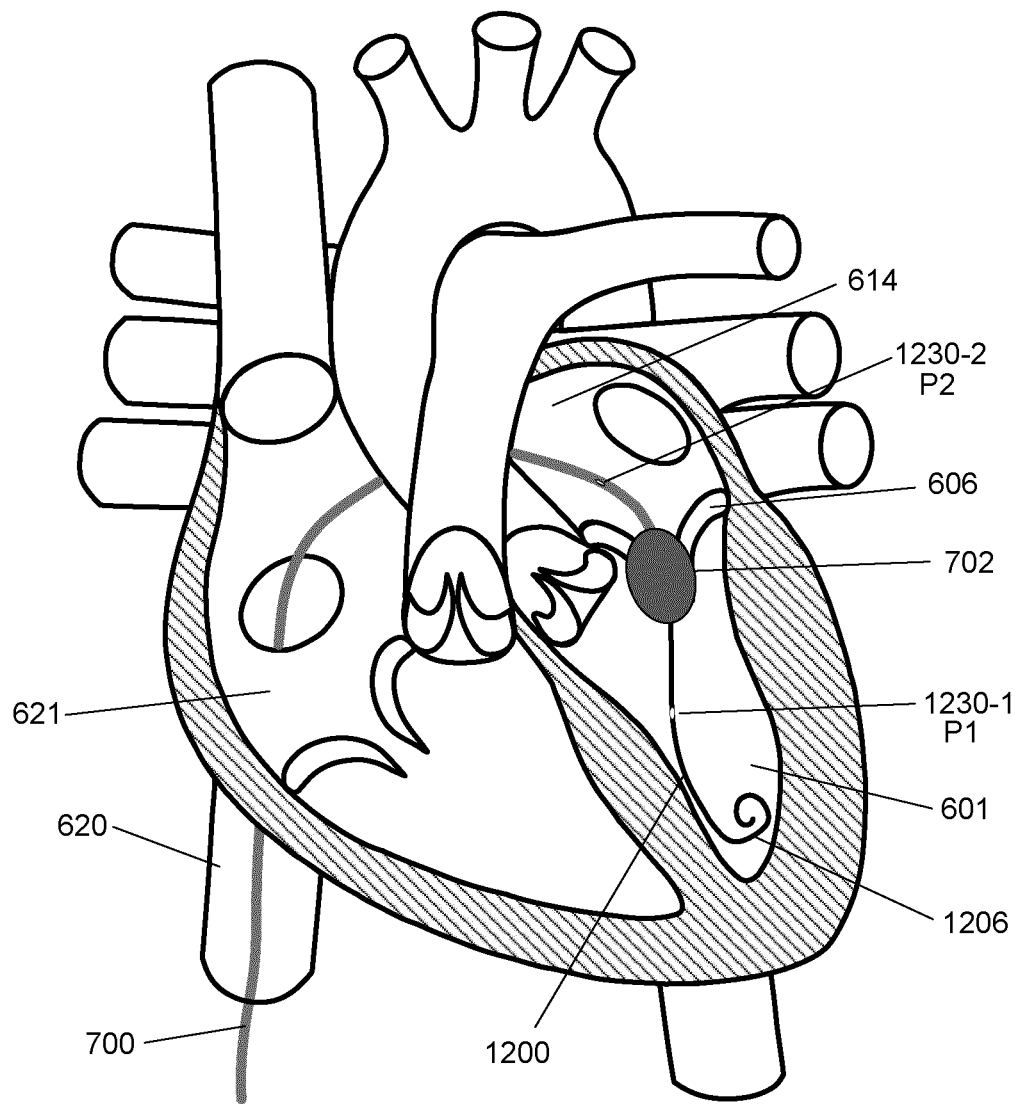
FIG. 19 shows a schematic partial cross-sectional diagram of a human heart to illustrate placement of the dual sensor support guidewire for measurements of hemodynamic parameters, including concurrent measurements of blood pressure in the LV and RA during TMVR (trans-septal approach)

FIG. 19 shows a schematic partial cross-sectional diagram 600-7 showing placement of a dual sensor support guidewire 1200 through the inferior vena cava 620 and the RA 621 for a trans-septal approach to the LA 614 and LV 601 for TMVR. In this example, the tip 1206 of the sensor support guidewire 1200 is positioned in the LV 601 for measurement of the LV pressure by pressure sensor 1230-1 (P1). Catheter 700 and valve delivery device 702 are mounted over the sensor support guidewire 1200 to position the valve delivery device through the mitral valve 606. The pressure in the left atrium 614 may be obtained by a second optical sensor 1230-2 (P2) in the sensor support guidewire 1200 positioned in the LA 614, i.e., measurements made before introducing or after withdrawing the valve delivery device 702. Alternatively, the LA pressure may be obtained indirectly from a pulmonary wedge pressure measurement made with a pulmonary artery (PA) catheter.

Regarding pressure ranges to be measured within the aorta and chambers of the heart, the peak pressure in the LV may be around 150 mmHg or more, so for absolute pressure measurements, pressure sensors capable of directly measuring blood pressure in the range of 0 to ~300 mmHg are suitable. For assessing heart valve function, accurate measurement of smaller differences in blood pressure is required to assess a transvalvular pressure gradient. For example, considering a transvalvular pressure gradient across the aortic valve, in a healthy heart, this pressure difference would be close to zero, or e.g., <5 mmHg. A pressure difference measured in the LV and ascending aorta (Ao) in the range of e.g., >40 mmHg to 60 mmHg, would be indicative of severe aortic valve stenosis. During TAVR to deploy a prosthetic aortic valve, if a measurement of the aortic transvalvular pressure gradient is made before and after deployment and positioning of a prosthetic aortic valve, if the valve deployment is successful, it would be expected to see a significant decrease in the transvalvular pressure gradient, e.g. from >40 mmHg to <10 mmHg if valve placement is optimal. For repositionable prosthetic valves, measurements of the transvalvular pressure gradient when the prosthetic valve is first positioned, and then repositioned to achieve a lower pressure gradient, may provide additional data to assist in optimal placement of the prosthetic valve. Thus, for TAVR, while measurement of transvalvular pressure gradients in the range of 0 to 60 mmHg within ±2 mmHg is desirable, measurement within ±10 mmHg may be adequate to assess aortic valve function before and after TAVR, e.g., to show a significant reduction in transvalvular pressure gradient from >40 mmHg before TAVR to <20 mmHg or <10 mmHg after deployment of prosthetic valve. To improve the accuracy of transvalvular pressure measurements with the pair of FP optical pressure sensors, it is beneficial if the first and second FP pressure sensors are "zeroed" relative to each other by taking simultaneous pressure measurements with both first and second FP optical pressure sensors placed within one chamber of the heart, e.g. with both sensors placed within the LV measuring the same pressure concurrently.

In comparison, for the mitral valve, it is required to measure a pressure gradient with greater accuracy. For example, a transvalvular pressure gradient of 20 mmHg would be indicative of severe mitral valve stenosis or other severe mitral valve malfunctioning. Thus, a mitral valve transvalvular pressure gradient of >5 mmHg may be indicative of mitral valve stenosis. For this reason, assessment of mitral valve function requires measurement of a transvalvular pressure gradient within ±2 mmHg, and preferably within ±1 mmHg is desirable. As mentioned above, to improve the accuracy of transvalvular pressure measurements, it is beneficial if the first and second FP pressure sensors are "zeroed" relative to each other by taking simultaneous baseline pressure measurements with both first and second FP sensors positioned within one chamber of the heart, if possible in the LA, or alternatively in the LV.

The optical pressure sensors 230 and 330 (P1 and P2) are preferably Fabry-Pérot (FP) Micro-Opto-Mechanical System (MOMS) sensors, such as those described by FISO Technologies (E. Pinet, "Pressure measurement with fiber-optic sensors: Commercial technologies and applications" 21st International Conference on Optical Fiber Sensors, edited by Wojtek J. Bock, Jacques Albert, Xiaoyi Bao, Proc. of SPIE Vol. 7753, (2011)). These optical pressure sensors comprise an optical fiber having a FP MOMS sensor at the sensor end of the fiber for sensing pressure. By way of example, for standard diameter optical fibers, each fiber has a diameter of 0.155 mm (0.006 inch) and each optical pressure sensor has a diameter of 0.260 mm (0.010 inch). FP optical pressure sensors capable of pressure measurements in a range suitable for medical applications and blood pressure measurements are also available from Opsens Inc.

For smaller fibers, e.g. 0.100 mm fibers, and smaller diameter sensors, the dimensions of the sensor lumen of the sensor catheter and the inside diameter of inner tubular layer of the sensor guidewire may be reduced in size accordingly.

Since the sensor guidewires and sensor catheters of the embodiments are intended for single-use only, preferably the optical connectors for connection to the control unit are standard low cost optical connectors. Similarly, the flexible tubing, and other connectors for the other ports are preferably standard materials and components, such as luer fittings or other medical standard fluid ports, as appropriate, which can be sterilized, and so that the sensor catheter and sensor guidewire can be provided in single-use sterile packaging, using conventional processes for packaging and sterilization of medical devices.

As mentioned above, it is desirable that the sensor guidewire has mechanical characteristics, such diameter, stiffness and torque characteristics, similar to a conventional support guidewire for TVT. The optical fiber and optical pressure sensor do not add significant stiffness to the sensor guidewire, and thus these characteristics are primarily determined by structure and materials of the sensor guidewire, e.g. the inner tubular layer which may be a stainless steel hypotube or polymer layer and the outer tubular layer which may be an outer stainless steel hypotube or stainless steel micro-coil or a combination thereof. The inner tubular layer may comprise a multilayer structure. Similarly, the outer tubular layer may also comprise a multilayer structure.

As mentioned above, it is desirable that the sensor catheter has mechanical characteristics, such diameter, stiffness and flexibility, similar to a conventional pig-tail catheter used for injection of contrast agent and other fluids. The optical fiber and optical pressure sensor do not add significant stiffness to the sensor catheter, and thus these characteristics are primarily determined by the type of material and wall thickness used for the multi-lumen catheter tubing.

Other factors for consideration are: regulatory requirements for medical devices, ease of use and safety. For these reasons, it is desirable that the materials for fabrication of sensor guidewire and sensor catheter are based on a conventional tried and tested medical devices, i.e. based on a predicate device structure which has regulatory approval and which is fabricated with materials and components which already have FDA and/or CE mark regulatory approval.

It will be appreciated that in alternative embodiments or variants of the dual sensor system of the embodiments described in detail above, different combinations of one or more features disclosed herein, and features disclosed in the related patent applications referenced herein, may provide further alternative embodiments.

As disclosed herein, in one embodiment, the cardiologist is offered dual sensor system comprising a TVT support guidewire containing a first optical pressure sensor (sensor support guidewire) and an angiographic pigtail catheter containing a second optical pressure sensor (sensor catheter), which has particular application for continuous blood pressure measurements during TVT, e.g. TAVR or TMVR, wherein the pair of optical pressure sensors are configured for monitoring and diagnostic measurements of hemodynamic parameters, including concurrent measurement of blood pressure at two different and variable locations within the heart and aorta during left heart catheterization. The interventional cardiologist may adjust the relative positioning of the sensor catheter and the sensor guidewire so that the first and second optical pressure sensors are positioned to suit the dimensions of an individual's heart, and are appropriately positioned for relative to the heart valve. Radiopaque markers on the sensor guidewire and sensor catheter may be provided to assist in positioning of the first and second FP optical sensors. A dual sensor system comprising single sensor guidewire used in conjunction with a single sensor catheter may offer a more cost-effective solution, which is more readily fabricated than multisensor guidewires and multisensor catheters.

If required a second sensor may be provided in a sensor guidewire. Thus, in another embodiment, a dual sensor system comprises a dual sensor guidewire for diagnostic measurements during left heart catheterization. The dual sensor guidewire may be used with the same two channel controller as described above.

In other applications of a TVT support guidewire containing a first FP optical pressure sensor, the TVT support guidewire is positioned for continuous direct measurement of LV pressure in the left ventricle during TVT, e.g. during TAVR or BAV. A second pressure measurement may be obtained using another type of pressure sensor placed in the ascending aorta, e.g. a fluid filled catheter with an external pressure sensor, or a catheter with an electrical pressure sensor. For TMVR, the pressure in the left atrium may be obtained indirectly by using a pulmonary artery (PA) catheter to obtain a pulmonary wedge pressure.

Systems and apparatus according to embodiments of the present invention described herein offer real-time hemodynamic valve function data to the cardiologist during TAVR. The first and second optical pressure sensors provide accurate measurements of blood pressure concurrently at two positions, i.e. in the left ventricle and in the ascending aorta. If required, the pressure measurements can be provided continuously, i.e. at any time throughout the TAVR procedure. In practice, pressure measurements may be made continually, e.g. periodically or at intervals before, during or after a TVT procedure. For example, the system enables uninterrupted monitoring of the LV pressure by the first sensor in the sensor support guidewire and the second pressure sensor in the sensor catheter can provide uninterrupted pressure measurements in the ascending aorta even during balloon valvuloplasty and valve deployment, when the part of the sensor guidewire downstream of the aortic valve is surrounded by a guide catheter, balloon catheter, valve delivery device or other components.

With the introduction of prosthetic valves that are repositionable during TVT, pressure measurements during TVT could potentially provide data on valve function at the point of deployment to assist in optimizing valve placement, to mitigate issues of sub-optimal valve placement, such as regurgitation or paravalvular leakage.

Advantageously, the sensor catheter has the external form and dimensions of a conventional pigtail catheter which is typically already in place in the aorta during TAVR, i.e. for delivery of contrast medium into the aorta and LV near the aortic valve. Externally, the sensor guidewire resembles a conventional support guidewire, having appropriate dimensions, stiffness and torque characteristics, and functionality to enable the sensor guidewire to be used in a conventional manner as a support guidewire for TAVR. Thus, apart from the need to make the optical connections for the sensor catheter and sensor guidewire to the control unit for activation of the optical pressure sensors, the sensor pigtail catheter can be introduced and used in same manner as a conventional angiographic pigtail catheter, and the sensor guidewire can be introduced and deployed in the same manner as a conventional support guidewire. Each of the sensors can provide pressure data continuously, or at intervals as needed during TAVR, without disrupting the standard TAVR procedure. With a suitably configured interface, the controller provides compatibility with standard PCM systems, and thus can be integrated more readily into the Cath Lab, with less equipment clutter, and avoiding additional cabling.

For some applications, such as diagnostic measurements to assess heart valve function, it may be desirable to provide a dual sensor guidewire, such as sensor guidewire 1200 described above. However, providing two or more optical pressure sensors within a support guidewire adds to cost and manufacturing complexity. Since a pigtail catheter is typically in place during TVT for delivery of contrast medium, providing one sensor in the pigtail catheter and one sensor in the support guidewire potentially offers a lower cost system. Further cost reductions are offered when the controller is configured to interface directly with standard operating room and Cath Lab monitoring systems, thereby avoiding the need for a dedicated stand-alone monitoring unit.

TABLE 2

| Abbreviations or acronyms | |
| --- | --- |
| ARi or AR Index | Aortic Regurgitation Index |
| BAV | Balloon Aortic Valvuloplasty |
| Cath Lab | Cardiac Catheterization Laboratory |
| CE Mark | 'Conformité Européenne', a European certification mark |
| DBP | Diastolic Blood Pressure |
| FP MOMS Sensor | Fabry-Pérot Micro-Opto-Mechanical-System Sensor |
| ICU | Intensive Care Unit |
| LVEDP | Left Ventricular End-Diastolic Pressure |
| OR | Operating Room |
| RA | Right Atrium |
| RV | Right Ventricle |
| SBP | Systolic Blood Pressure |
| TAVI or TAVR | Transcatheter Aortic Valve Implantation or Replacement |
| TMVI or TMVR | Transcatheter Mitral Valve Implantation or Replacement |
| TVR | Transcatheter heart Valve Replacement |
| TVT | Transcatheter Valve Therapies |
| LV | Left Ventricle |
| LA | Left Atrium |
| FDA | Food and Drug Administration |
| EEPROM | Electrically Erasable Programmable Read-Only Memory |
| AAMI | Association for the Advancement of Medical Instrumentation |
| ANSI | American National Standards Institute |
| ANSI BP-22 | Standards document ANSI/AAMI BP22: 1994/(R)2016 relating to performance and safety requirements for transducers, including cables, designed for blood pressure measurements through an indwelling catheter or direct puncture. |

INDUSTRIAL APPLICABILITY

Dual sensor systems comprising sensor catheters and sensor guidewires according to embodiments disclosed herein are configured to provide real-time, concurrent, pressure measurements at two locations during TAVR, other TVT procedures and for diagnostic measurements of hemodynamic parameters to assess heart function. A pair of optical pressure sensors enables two pressure measurements to be taken concurrently, i.e. using similar FP optical pressure sensors in the both a sensor catheter and a sensor support guidewire. For example, the sensor guidewire has the same physical characteristics, such as stiffness, of a support guidewire for TAVR, and the sensor catheter has the form of an angiographic catheter which is conventionally placed in the aorta for injection of contrast medium. Blood pressure measurements can be obtained continually during TAVR by placement of the sensor guidewire to position the first optical pressure sensor in the LV for LV pressure monitoring, and placement of the sensor catheter to position the second optical pressure sensor within the aorta downstream of the aortic valve for Aortic pressure monitoring. Pressure measurements may be made continuously or at intervals on demand during TAVR. The controller may be configured to interface directly with ANSI BP-22 compliant patient monitoring systems. For some applications, a dual sensor support guidewire is provided.

Although embodiments of the invention have been described and illustrated in detail, it is to be clearly understood that the same is by way of illustration and example only and not to be taken by way of limitation, the scope of the present invention being limited only by the appended claims.

The invention claimed is:

1. A dual sensor system for monitoring blood pressure at first and second locations within a heart and blood vessels of a patient during transcatheter valve therapy (TVT), comprising:
a controller;
a sensor support guidewire for TVT comprising a tubular member having a length extending between a proximal end and a distal end of the tubular member, the distal end comprising an atraumatic pre-formed curved flexible distal tip, the tubular member containing a first optical fiber extending within the sensor support guidewire from an optical input/output connector at the proximal end of the sensor support guidewire to a first Fabry-Pérot (FP) optical pressure sensor, the first FP optical pressure sensor being positioned within a distal region of the tubular member, near the flexible distal tip, and a first sensor aperture in the sensor support guidewire adjacent the first FP optical pressure sensor for fluid contact therewith;
a sensor angiographic catheter comprising multi-lumen catheter tubing having a length extending between a proximal end and a distal end of the multi-lumen catheter tubing and comprising a first lumen and a second lumen, the distal end comprising a preformed pigtail distal tip, and the catheter tubing having at its proximal end a connection hub comprising a first port for the first lumen and a second port for the second lumen, a second optical fiber extending within the first lumen from an optical/input output connector of the first port to a second FP optical pressure sensor, the second FP optical pressure sensor being positioned within a distal region of the first lumen near the pigtail distal tip, and a second sensor aperture in the first lumen of the catheter tubing near the second FP optical pressure sensor for fluid contact therewith; the second port comprising an injection port for injection of fluid into the second lumen, and the second lumen comprising a plurality of apertures for fluid ejection along a length of the distal region between the second sensor aperture and the pigtail distal tip;
the controller comprising an optical control unit comprising optical input/output ports for coupling to the optical input/output connectors of the sensor support guidewire and the sensor angiographic catheter and a light source and detector for operating the first and the second FP optical pressure sensors and processing optical data from the first and the second FP optical pressure sensors to generate data indicative of blood pressure; a processor, memory, hardware and/or software components for generating at least one of analog and digital data comprising first and second pressure waveforms; and a communications interface comprising ports for interfacing with at least one of a patient monitoring system and other peripherals providing data storage and display.

2. The dual sensor system of claim 1, configured for measurements of hemodynamic parameters in a left ventricle and ascending aorta of the patient during Transcatheter Aortic Valve Replacement (TAVR), wherein:
the flexible distal tip of the sensor support guidewire comprises a preformed curved tip configured for positioning within the left ventricle; the first FP optical pressure sensor (P1) is a distance L1 from the flexible distal tip of the sensor support guidewire for positioning of P1 within the left ventricle during TAVR; and
the sensor angiographic catheter comprises a dual lumen pigtail catheter wherein said plurality of apertures in the second lumen near the pigtail distal tip are arranged for injection of contrast medium into the ascending aorta, and the second FP optical pressure sensor (P2) is located in the distal region of the first lumen of the sensor angiographic catheter a distance L2 from the pigtail distal tip for positioning of P2 in the ascending aorta, downstream of an aortic valve, during TAVR.

3. The dual sensor system of claim 2, wherein the first and the second FP optical pressure sensors are a pair of FP optical pressure sensors configured for measuring a blood pressure gradient across the aortic valve during TAVR in a range of 0 mmHg to 60 mmHg with an accuracy of ±10 mmHg or less.

4. The dual sensor system of claim 1, configured for measurements of hemodynamic parameters of the patient during Transcatheter Mitral Valve Replacement (TMVR), wherein:
the first FP optical pressure sensor (P1) is located a distance L1 from the flexible distal tip of the sensor support guidewire for positioning of P1 within a first heart chamber on one side of a mitral valve during TMVR;
the second FP optical pressure sensor (P2) is located in the first lumen of the sensor angiographic catheter a distance L2 from the pigtail distal tip for positioning of P2 in a second heart chamber, on an opposite side of the mitral valve during TMVR; and said plurality of apertures in the second lumen near the pigtail distal tip are arranged for injection of contrast medium into the second heart chamber.

5. The dual sensor system of claim 4 wherein the first and the second FP optical pressure sensors are a pair of FP optical pressure sensors configured for measuring a blood pressure gradient across the mitral valve during TMVR in a range of 0 mmHg to 20 mmHg with an accuracy of ±2 mmHg or less.

6. The dual sensor system of claim 1, wherein the sensor support guidewire has stiffness characteristics along its length configured for mounting of a prosthetic valve delivery device over the sensor support guidewire, wherein stiffness characteristics of a distal region of the sensor support guidewire that supports the prosthetic valve delivery device during prosthetic valve deployment are in a range of stiffness characteristics of support guidewires of a group comprising a Safari™ guidewire, a Confida™ guidewire and an Amplatz™ Super Stiff Guidewire.

7. The dual sensor system of claim 1, wherein the sensor support guidewire has stiffness characteristics along its length configured for mounting of a prosthetic valve delivery device over the sensor support guidewire, wherein stiffness characteristics of a distal region of the sensor guidewire that supports the prosthetic valve delivery device during prosthetic valve deployment are defined by a flexural modulus in a range of 17 GPa to 158 GPa.

8. The dual sensor system of claim 1, wherein the sensor support guidewire has a maximum outside diameter of ≤0.89 mm (0.035 inch) and a length in a range from 1 m to 3 m.

9. The dual sensor system of claim 1, wherein the optical input/output connector of the first port of the sensor angiographic catheter comprises a separable optical connector and a flexible optical coupling comprising a length of optical cable, the separable optical connector detachably connecting the sensor angiographic catheter to one end of the optical cable, and the optical cable having at its other end an optical connector for connection to the controller.

10. The dual sensor system of claim 1, wherein the optical input/output connector at the proximal end of the sensor support guidewire comprises a separable optical connector and a flexible optical coupling comprising a length of optical cable, the separable optical connector detachably connecting the sensor support guidewire to one end of the optical cable, and the optical cable having at its other end an optical connector for connection to the controller.

11. The dual sensor system of claim 10, wherein for mounting of TVT components over the sensor support guidewire from the proximal end of the sensor support guidewire, the separable optical connector comprises an optical micro-connector having a male part and a female part, wherein the sensor support guidewire comprises the male part of the optical micro-connector, the male part having a diameter no greater than a maximum outside diameter the sensor support guidewire.

12. The dual sensor system of claim 11, wherein the flexible optical coupling comprises the female part of the optical micro-connector, which forms a connector handle for manipulating the sensor support guidewire.

13. The dual sensor system of claim 1, wherein the sensor support guidewire comprise a first radiopaque marker near the first FP optical pressure sensor, and the sensor angiographic catheter comprises a second radiopaque marker near the second FP optical sensor and the pigtail distal tip, and optionally, additional radiopaque markers are placed at regular intervals along the length of the sensor angiographic catheter and sensor support guidewire, so that, in use, relative positioning or spacing of the first and the second FP optical pressure sensors of the sensor angiographic catheter and the sensor support guidewire can be determined.

14. The controller for the dual sensor system of claim 1, comprising: an optical control unit comprising a light source and detector, and an optical interface for coupling, via respective optical input/output ports, to each of the optical input/output connectors of the sensor support guidewire containing the first FP optical pressure sensor and the sensor angiographic catheter containing the second FP optical pressure sensor; data storage and processing means configured for processing optical data indicative of pressure values, and outputting at least one of digital and analog signals to ports of a communications interface, for coupling to a patient monitoring system and other peripherals for data storage and display.

15. The controller of claim 14, for connection to a patient monitoring system comprising a patient care monitor (PCM) configured for receiving analog signals indicative of blood pressure compliant with an ANSI BP-22 Standard, the controller comprises a BP-22 signal converter, and wherein the communications interface comprises ports for respective analog signal outputs from each of the first and the second FP optical pressure sensors and analog control signal inputs.

16. A sensor support guidewire for use in dual sensor system for monitoring blood pressure at first and second locations within a heart and blood vessels of a patient during transcatheter valve therapy (TVT) using a first Fabry Pérot (FP) optical pressure sensor contained within the sensor support guidewire and a second FP optical pressure sensor contained within a sensor angiographic catheter, the sensor support guidewire comprising a tubular member having a length extending between a proximal end and a distal end of the tubular member, the distal end comprising a flexible distal tip, the tubular member comprising an outer tubular member and an inner tubular member, the inner tubular member inserted within the outer tubular member, and an optical fiber extending within the inner tubular member from an optical input/output connector at the proximal end of the sensor support guidewire to the first FP optical pressure sensor, the first FP optical pressure sensor being positioned within a distal region of the sensor support guidewire, near the flexible distal tip, a first sensor aperture in the tubular member adjacent the first FP optical pressure sensor for fluid contact therewith, and the flexible distal tip comprising a pre-formed curved tip.

17. The sensor support guidewire of claim 16, wherein the inner tubular member comprises a first stainless steel hypotube having physical characteristics providing a predetermined stiffness and flexibility to act as a core of the TVT sensor support guidewire and the outer tubular member comprises one of a second stainless steel hypotube, a flexible spiral wound micro-coil, and a combination thereof.

18. The sensor support guidewire of claim 17, wherein the inner tubular member acts as the core to provide a required stiffness along the length of the sensor support guidewire, and the outer tubular member is more flexible than the inner tubular member along at least part of the length of the outer tubular.

19. The sensor support guidewire of claim 16, wherein, the first sensor aperture comprises an outer sensor aperture in the outer tubular member and an inner sensor aperture in the inner tubular member, the outer tubular member comprising a reinforced stiffer region around the outer sensor aperture.

20. The sensor support guidewire of claim 16, wherein the first sensor aperture comprises an outer sensor aperture in the outer tubular member, and a region of the inner tubular member, wherein said region is partially cut away to form a cavity around the first FP optical pressure sensor, the outer tubular member comprising a reinforced stiffer region extending around the outer sensor aperture.

21. The TVT sensor support guidewire of claim 16, further comprising an additional FP optical pressure sensor and an additional optical fiber contained within the inner tubular member, the additional FP optical pressure sensor being positioned proximally of the first FP optical pressure sensor, and wherein the inner tubular member has an aperture adjacent the additional FP optical pressure sensor, or is partially cut away to form a cavity around the additional FP optical pressure sensor, and the outer tubular member comprises an additional sensor aperture adjacent the additional FP optical pressure sensor and a reinforced region around the additional sensor aperture adjacent the additional sensor.

22. The sensor support guidewire of claim 21, wherein the first and the second FP optical pressure sensors are spaced apart by a distance L in a range from 20 mm to 100 mm.

23. The sensor support guidewire of claim 16, having stiffness characteristics along its length similar to stiffness characteristics of a TVT support guidewire comprising one of a Safari™ guidewire, a Confida™ guidewire and an Amplatz™ Super Stiff guidewire.

24. A sensor angiographic catheter for use in dual sensor system for monitoring blood pressure at first and second locations within a heart and blood vessels of a patient during transcatheter valve therapy (TVT) using a first Fabry Pérot (FP) optical pressure sensor contained within a sensor support guidewire and a second FP optical pressure sensor contained within the sensor angiographic catheter, the sensor angiographic catheter comprising multi-lumen catheter tubing having a length extending between a proximal end and a distal end of the multi-lumen catheter tubing and comprising a first lumen and a second lumen, the distal end comprising a preformed pigtail distal tip, and the catheter tubing having at its proximal end a connection hub comprising a first port for the first lumen and a second port for the second lumen, an optical fiber extending within the first lumen from an optical/input output connector of the first port to the second FP optical pressure sensor, the second FP optical pressure sensor being positioned within a distal region of the first lumen near the distal tip, and a sensor aperture in the sensor angiographic catheter near the second FP optical pressure sensor for fluid contact therewith; and the second port comprising an injection port for injection of fluid and the second lumen comprising a plurality of apertures for fluid ejection along a length of the distal region near the pigtail distal tip between the sensor aperture and the distal tip.

25. The sensor angiographic catheter of claim 24 wherein the multi-lumen catheter tubing comprises dual lumen tubing having an outside diameter in a range from 4 French to 7 French, wherein the first lumen is sized to accommodate the optical fiber and the second FP optical pressure sensor and the second lumen is sized for rapid injection of contrast medium.

26. The sensor angiographic catheter of claim 25, wherein the second lumen is sized to act as a guidewire lumen for insertion of the sensor angiographic catheter over a guidewire.

27. The sensor angiographic catheter of claim 24, wherein the catheter tubing further comprises one or more additional lumens, and the connection hub further comprises a corresponding number of additional ports.

28. The sensor angiographic catheter of claim 24, further comprising a first radiopaque marker near the second FP optical pressure sensor and a second radiopaque marker at the distal tip of the sensor angiographic catheter.

29. A kit comprising components for use with a dual sensor system for monitoring blood pressure at first and second locations within a heart and blood vessels of a patient during transcatheter valve therapy (TVT), comprising:

a first component comprising: a sensor support guidewire for TVT comprising a tubular member having a length extending between a proximal end and a distal end of the tubular member, the distal end comprising an atraumatic pre-formed curved flexible distal tip, the tubular member containing a first optical fiber extending within the sensor support guidewire from an optical input/output connector at the proximal end of the sensor support guidewire to a first Fabry-Pérot (FP) optical pressure sensor, the first FP optical pressure sensor being positioned within a distal region of the tubular member, near the flexible distal tip, and a first sensor aperture in the sensor support guidewire adjacent the first FP optical pressure sensor for fluid contact therewith;

a second component comprising: a sensor angiographic catheter comprising multi-lumen catheter tubing having a length extending between a proximal end and a distal end, and comprising a first lumen and a second lumen, the distal end comprising a preformed pigtail distal tip, and the catheter tubing having at its proximal end a connection hub comprising a first port for the first lumen and a second port for the second lumen, a second optical fiber extending within the first lumen from an optical/input output connector of the first port to a second FP optical pressure sensor, the second FP optical pressure sensor being positioned within a distal region of the first lumen near the pigtail distal tip, and a second sensor aperture in first lumen of the catheter tubing near the second FP optical pressure sensor for fluid contact therewith; the second port comprising an injection port for injection of fluid into the second lumen, and the second lumen comprising a plurality of fluid apertures along a length of the distal region between the second sensor aperture and the pigtail distal tip; and wherein the first and the second FP optical pressure sensors are a pair of FP optical pressure sensors.

30. The kit of claim 29, wherein
the optical input/output connector of the first port of the sensor angiographic catheter comprises a separable optical connector and a flexible optical coupling comprising a length of optical cable, the separable optical connector detachably connecting the sensor angiographic catheter to one end of the optical cable, and the optical cable having at its other end an optical connector for connection to controller; and the optical input/output connector at the proximal end of the sensor support guidewire comprises a separable optical connector and a flexible optical coupling comprising a length of optical cable, the separable optical connector detachably connecting the sensor support guidewire to one end of the optical cable, and the optical cable having at its other end an optical connector for connection to the controller; and wherein for over-the-guidewire mounting of components from the proximal end of the sensor support guidewire, the separable optical connector comprises an optical micro-connector having a male part and a female part, wherein the sensor support guidewire carries the male part of the optical micro-connector, wherein said male part has a diameter no greater than a maximum outside diameter of the sensor support guidewire, and the flexible optical coupling carries the female part of the optical micro-connector, said female part forming a connector handle for manipulating the sensor support guidewire.

31. The kit of claim 29 wherein the first and the second FP optical pressure sensors are configured for measuring a transvalvular blood pressure gradient across an aortic valve during TAVR in a range of 0 mmHg to 60 mmHg with an accuracy of ±10 mmHg or less.

32. The kit of claim 29 wherein first and second FP optical pressure sensors are configured for measuring a transvalvular blood pressure gradient across a mitral valve during TMVR in a range of 0 mmHg to 20 mmHg with an accuracy of ±2 mmHg or less.

* * * * *

UNITED STATES PATENT AND TRADEMARK OFFICE
CERTIFICATE OF CORRECTION

PATENT NO. : 11,406,271 B2
APPLICATION NO. : 16/764119
DATED : August 9, 2022
INVENTOR(S) : Tom Glawdel et al.

Page 1 of 1

It is certified that error appears in the above-identified patent and that said Letters Patent is hereby corrected as shown below:

In the Claims

Column 32, Line 56: "guidewire that" should read -- support guidewire that --

Column 34, Line 23: "tubular." should read -- tubular member. --

Column 34, Line 37: "The TVT sensor" should read -- The sensor --

Signed and Sealed this
Twenty-seventh Day of December, 2022

Katherine Kelly Vidal
*Director of the United States Patent and Trademark Office*